(12) United States Patent
Iguchi et al.

(10) Patent No.: US 10,974,061 B2
(45) Date of Patent: Apr. 13, 2021

(54) OPTICAL TREATMENT APPARATUS AND FIXING TOOL

(71) Applicant: SHARP KABUSHIKI KAISHA, Sakai (JP)

(72) Inventors: Katsuji Iguchi, Sakai (JP); Hiroya Sato, Sakai (JP); Takashi Yoshimoto, Sakai (JP); Jun Mori, Sakai (JP)

(73) Assignee: SHARP KABUSHIKI KAISHA, Sakai (JP)

( * ) Notice: Subject to any disclaimer, the term of this patent is extended or adjusted under 35 U.S.C. 154(b) by 185 days.

(21) Appl. No.: 16/304,301

(22) PCT Filed: May 19, 2017

(86) PCT No.: PCT/JP2017/018764
§ 371 (c)(1),
(2) Date: Nov. 25, 2018

(87) PCT Pub. No.: WO2017/204093
PCT Pub. Date: Nov. 30, 2017

(65) Prior Publication Data
US 2019/0083806 A1    Mar. 21, 2019

(30) Foreign Application Priority Data
May 27, 2016   (JP) .............................. JP2016-106736

(51) Int. Cl.
*A61N 5/06*    (2006.01)
*A61B 90/40*   (2016.01)
(Continued)

(52) U.S. Cl.
CPC .............. *A61N 5/06* (2013.01); *A61B 90/40* (2016.02); *A61F 13/00* (2013.01);
(Continued)

(58) Field of Classification Search
None
See application file for complete search history.

(56) References Cited

U.S. PATENT DOCUMENTS 5,520,177 A * 5/1996 Ogawa ............... A61B 5/14552
600/323
2004/0166146 A1 * 8/2004 Holloway ............ A61N 5/0616
424/449

(Continued)

FOREIGN PATENT DOCUMENTS

CN        2714088 Y      8/2005
CN       105209113 A    12/2015
(Continued)

*Primary Examiner* — Kennedy Schaetzle
(74) *Attorney, Agent, or Firm* — ScienBiziP, P.C.

(57) ABSTRACT

An optical treatment apparatus includes: a power source unit; a light irradiation module, that irradiates an affected part with light; a spacer that is positioned between the light irradiation module and the affected part; a fixing material that applies pressure to the light irradiation module and fixes the light irradiation module at an installation position; and a shielding material that covers the light irradiation module, in which, in a case where the pressure applied by the fixing material becomes lower than predetermined pressure, supply of current is stopped.

18 Claims, 17 Drawing Sheets

(51) Int. Cl.
*A61F 13/00* (2006.01)
*A61B 90/00* (2016.01)
*A61B 17/00* (2006.01)
*A61B 18/00* (2006.01)

(52) U.S. Cl.
CPC ............... *A61B 2017/0003* (2013.01); *A61B 2018/00708* (2013.01); *A61B 2018/00791* (2013.01); *A61B 2090/065* (2016.02); *A61F 2013/00655* (2013.01); *A61F 2013/00846* (2013.01); *A61N 2005/0626* (2013.01); *A61N 2005/0645* (2013.01); *A61N 2005/0651* (2013.01)

(56) References Cited

U.S. PATENT DOCUMENTS

| | | | |
|---|---|---|---|
| 2007/0239233 A1* | 10/2007 | Klein | A61N 5/0616 607/88 |
| 2008/0281307 A1 | 11/2008 | Donahue | |
| 2010/0010593 A1 | 1/2010 | Wagennar Cacciola et al. | |
| 2010/0152719 A1* | 6/2010 | Fujikawa | A61B 18/203 606/9 |
| 2013/0144364 A1* | 6/2013 | Wagenaar Cacciola | A61N 5/0625 607/90 |
| 2014/0074191 A1* | 3/2014 | Dunleavy | A61N 1/28 607/88 |
| 2015/0045843 A1* | 2/2015 | Asah | A61N 5/0616 607/3 |
| 2015/0165231 A1* | 6/2015 | Scheja | A61N 5/062 604/20 |
| 2015/0238774 A1* | 8/2015 | Anderson | A61F 13/0213 604/20 |
| 2015/0290470 A1 | 10/2015 | Tapper et al. | |

FOREIGN PATENT DOCUMENTS

| | | |
|---|---|---|
| JP | H09-201422 A | 8/1997 |
| JP | 2003-290368 A | 10/2003 |
| JP | 2005-224505 A | 8/2005 |
| JP | 2010-500076 A | 1/2010 |
| WO | 2001/014012 A1 | 3/2001 |
| WO | 2012/023086 A1 | 2/2012 |

* cited by examiner

2: AFFECTED PART

12: SPACER
13: LIGHT IRRADIATION MODULE
20: LIGHT EMITTING UNIT
21: SENSOR UNIT
22A: ANODE WIRE
22C: CATHODE WIRE
22I: INTER-CHIP WIRE
23: BONDING WIRE
24: LED CHIP
25: FIRST FLEXIBLE SUBSTRATE
27: FIRST PROTECTION FILM
28A: ANODE EXTERNAL CONNECTION UNIT
29: FIRST WIRE LAYER
30: SECOND FLEXIBLE SUBSTRATE
31: SECOND WIRE LAYER
32: THERMISTOR
33: SECOND PROTECTION FILM
34C: SENSOR OUTPUT

20: LIGHT EMITTING UNIT
22A: ANODE WIRE
22AT: ANODE TERMINAL
22AV: ANODE VERTICAL WIRE
22C: CATHODE WIRE
22CT: CATHODE TERMINAL
22CV: CATHODE VERTICAL WIRE
22I: INTER-CHIP WIRE
23: BONDING WIRE
24: LED CHIP
25: FIRST FLEXIBLE SUBSTRATE
26: DUMMY PATTERN
28A: ANODE EXTERNAL CONNECTION UNIT
28C: CATHODE EXTERNAL CONNECTION UNIT

1: BODY
2: AFFECTED PART
4: POWER SOURCE UNIT
10: POCKET
11A: FIXING MATERIAL
12: SPACER
13: LIGHT IRRADIATION MODULE
14: SHIELDING MATERIAL
15: COOLING MATERIAL
16: SIGNAL LINE
35A, 35F: TERMINAL
40: POWER SOURCE UNIT POCKET
50: CONDUCTIVE UNIT
61: HOOK-AND-LOOP FASTENER (LOOP)
62: HOOK-AND-LOOP FASTENER (HOOK)
100A: OPTICAL TREATMENT APPARATUS

1: BODY
2: AFFECTED PART
4: POWER SOURCE UNIT
11B: FIXING MATERIAL
12: SPACER
13: LIGHT IRRADIATION MODULE
14: SHIELDING MATERIAL
15: COOLING MATERIAL
16: SIGNAL LINE
35A, 35F: TERMINAL
40: POWER SOURCE UNIT POCKET
50: CONDUCTIVE UNIT
61: HOOK-AND-LOOP FASTENER (LOOP)
62: HOOK-AND-LOOP FASTENER (HOOK)
100B: OPTICAL TREATMENT APPARATUS

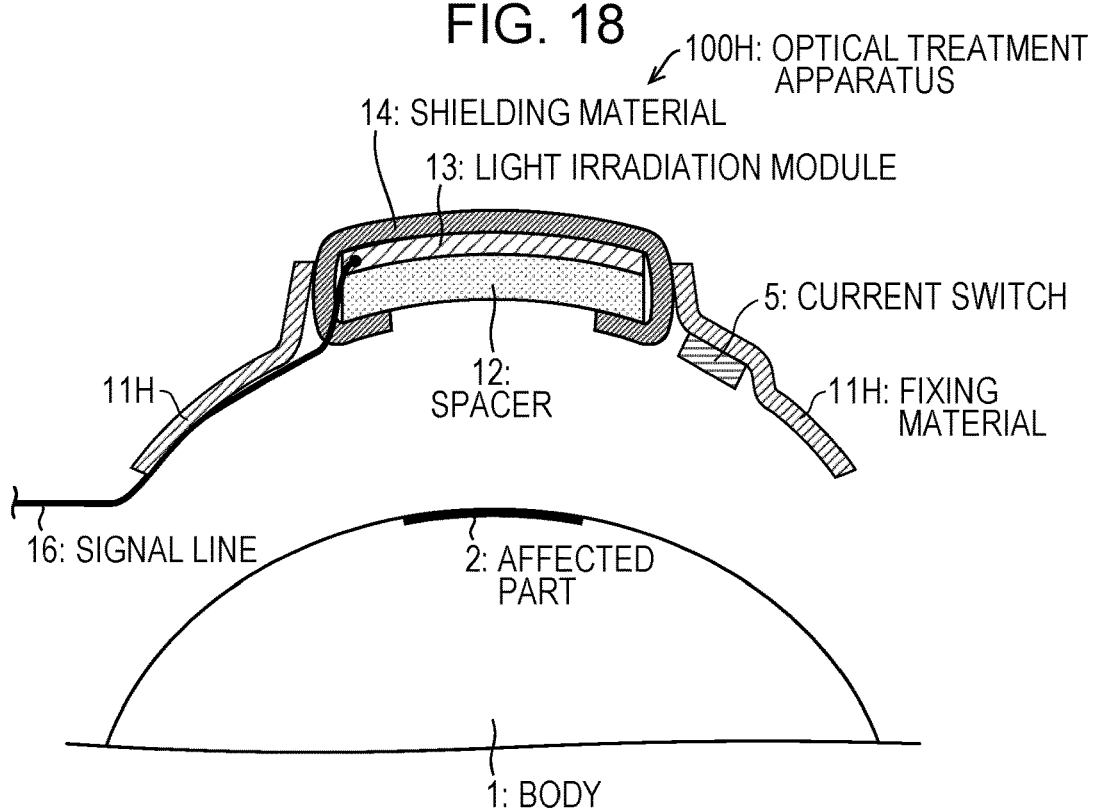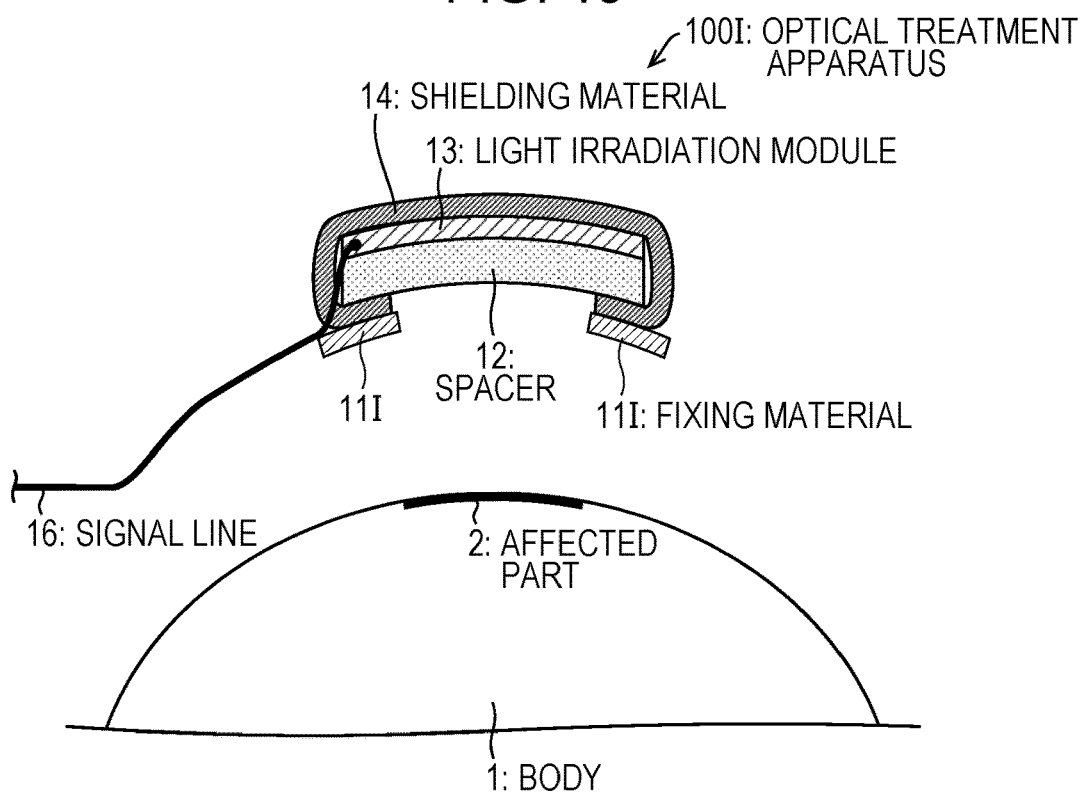

OPTICAL TREATMENT APPARATUS AND FIXING TOOL

TECHNICAL FIELD

The present invention relates to an optical treatment apparatus used for light irradiation therapy.

BACKGROUND ART

Light irradiation is utilized for various purposes including treatment for disease such as neonatal jaundice, psoriasis, or acne, alleviation of pain, and cosmetics. Specifically, green light and blue-white light are used for treatment for neonatal jaundice, ultraviolet light is used for treatment for psoriasis, and blue light, red light, and yellow light are used for treatment for acne. In this manner, various light sources are used in accordance with intended use.

For example, in a case of a light source such as an excimer lamp or an arc lamp, therapeutic light is radiated to an affected part arranged at a constant distance from the fixed light source. However, in a case where such a light source of a lamp type is used, an irradiation area is too large and a part other than an affected part is also irradiated with therapeutic light, so that there is a concern about various side effects on a normal part. Thus, some shielding countermeasures need to be taken to prevent the irradiation to the normal part with therapeutic light, and treatment takes time and effort.

For example, in a case where disease developed in a part of a face is treated, a mask for eyes (blindfold) with which eyes that are normal parts are protected is necessary, and, furthermore, a mask which exposes only an affected part of the face is also necessary to protect normal parts of the face. Moreover, for the treatment, a patient is required to keep his/her posture almost without moving for several tens of minutes in a state where his/her body is restrained, and such an experience is not pleasant even for the treatment.

In a case where an affected part has a curved surface, for example, like an arm or a foot, depending on a part such as a front part, a rear part, or a side part, an irradiating apparatus of a lamp type may force a patient to take an unnatural posture. In addition, irradiation intensity is different for each position of the affected part depending on an angle or a distance of the affected part having the curved part with respect to the lamp, so that it is difficult to irradiate an entirety of the affected part with uniform therapeutic light in some cases. Further, the apparatus using such a light source of the lamp type has many accompanying devices such as a power source and a cooling device and is large-sized, so that a large space is required for installation and a price of the apparatus becomes high.

Under such circumstances, some techniques by which light irradiation is able to be performed with an affected part directly covered have been proposed. For example, PTL 1 discloses an optical treatment apparatus which has flexibility and in which a large number of LEDs serving as light-emitting light sources are arranged on a flexible substrate and the resultant is wound around an affected part to perform light irradiation. PTL 2 discloses an optical treatment apparatus in which an LED serving as a light source is arranged on a flexible substrate and a light-transmitting material is held between an affected part and the LED so that light emitted from the LED is able to be transmitted to the affected part.

CITATION LIST

Patent Literature

PTL 1: International Publication No. WO2001/014012 (published on Mar. 1, 2001)

PTL 2: International Publication No. WO2012/023086 (published on Feb. 23, 2012)

SUMMARY OF INVENTION

Technical Problem

However, related arts described above have the following problems.

That is, in PTL 1, since the light sources are integrated with a fixing tool that fixes the light sources to the affected part, apparatuses of different sizes according to treatment parts such as a trunk, an arm, and a thigh need to be made. In general, a treatment part often has a small area, and, in such a case, skin with a considerable area around the treatment part is subjected to light irradiation. No problem arises when light irradiation intensity is weak and treatment is performed over a long time, however, when light intensity is increased to shorten a treatment time, there is a concern about a side effect on a normal part. Further, the light sources and the fixing tool need to be sterilized for each treatment. The light sources are able to be cooled by circulation of cooling water, and therefore a circulation apparatus for the cooling water is necessary, so that apparatus costs increase, in addition to restraint on a patient during treatment. Since a power source by which the light sources emit light is also provided separately and is connected to a light irradiation unit by a power cable, it is difficult for the patient to move around freely during treatment.

In PTL 2, no countermeasure against temperature of the light source is taken and there is no consideration about how to make the patient less restrained by a power source or a control unit. When light irradiation intensity is increased to shorten a treatment time, power consumption is increased, so that a problem of a temperature rise of skin also arises.

The invention is made in view of the aforementioned problems and an object thereof is to achieve an optical treatment apparatus capable of light irradiation therapy that allows reduction of burden on a patient or a medical practitioner, and that is safe and requires less labor.

Solution to Problem

In order to solve the aforementioned problems, an optical treatment apparatus according to an aspect of the invention includes: a power source unit; a light irradiation module that irradiates a target with light when current is supplied from the power source unit; a transparent spacer that is positioned between the light irradiation module and the target; a fixing material that applies predetermined pressure so as to press the light irradiation module against the transparent spacer and fixes the light irradiation module at an installation position; and a light shielding unit that is provided between the light irradiation module and the fixing material and covers the light irradiation module, in which, in a case where pressure applied by the fixing material becomes lower than the predetermined pressure, the supply of the current is stopped.

In order to solve the aforementioned problems, an optical treatment apparatus according to an aspect of the invention includes: a power source unit; a light irradiation module that irradiates a target with light when current is supplied from the power source unit; a transparent spacer that is positioned between the light irradiation module and the target; a fixing material that fixes the light irradiation module and the transparent spacer to be on the target; and a light shielding unit that covers the light irradiation module and the transparent spacer, in which, in a case where the light irradiation module is removed from the target, the supply of the current is stopped.

In order to solve the aforementioned problems, fixing tool according to an aspect of the invention includes: a fixing material that applies predetermined pressure to a light irradiation module that irradiates a target with light; and a light shielding unit that covers the light irradiation module, in which the fixing material includes a convex portion on an opposite side of the target, a space is formed by the light shielding unit and the convex portion, and the convex portion is provided with an opening that is openable or closeable.

Advantageous Effects of Invention

According to an aspect of the invention, an optical treatment apparatus capable of light irradiation therapy that allows reduction of burden on a patient or a medical practitioner, and that is safe and requires less labor is achieved.

BRIEF DESCRIPTION OF DRAWINGS

FIG. 18 is a sectional view illustrating a state where a modified example of the optical treatment apparatus is mounted on the body, in a divided manner.

FIG. 19 is a sectional view illustrating a state where an optical treatment apparatus according to Embodiment 9 is mounted on the body, in a divided manner.

DESCRIPTION OF EMBODIMENTS

Embodiments of the invention will be described in detail below. Note that, for convenience of description, a member having the same function as that of a member indicated in each embodiment will be given the same reference sign and description thereof will be omitted as appropriate.

Embodiment 1

Figure 1:
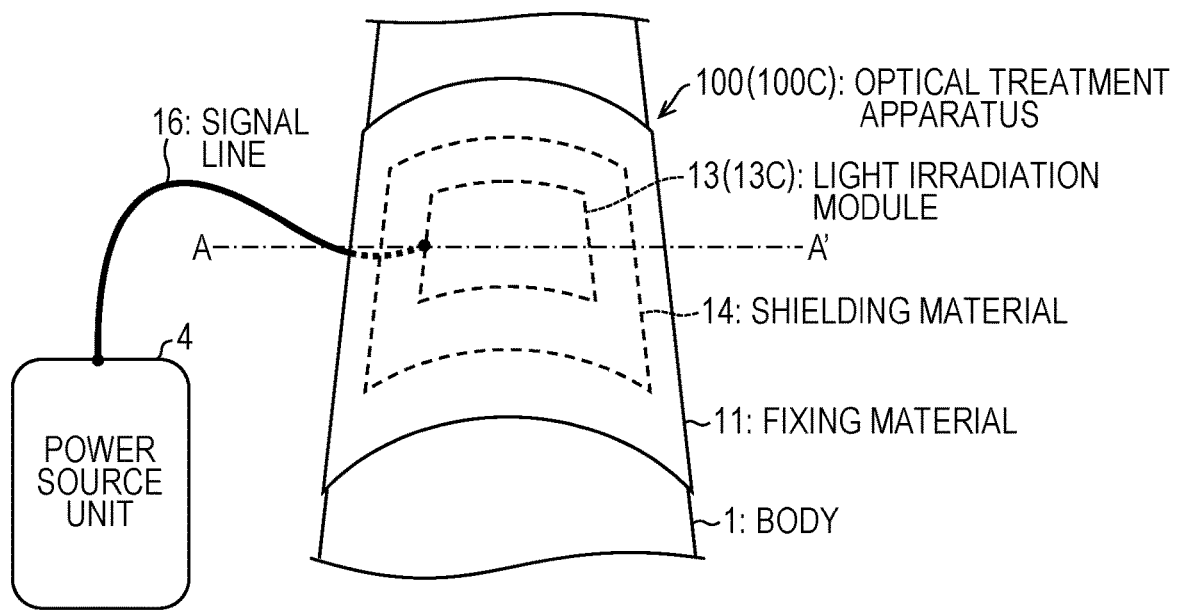
FIG. 1 is a bird's eye view illustrating a state where an optical treatment apparatus according to Embodiment 1 is mounted on a body.
Figure 2:
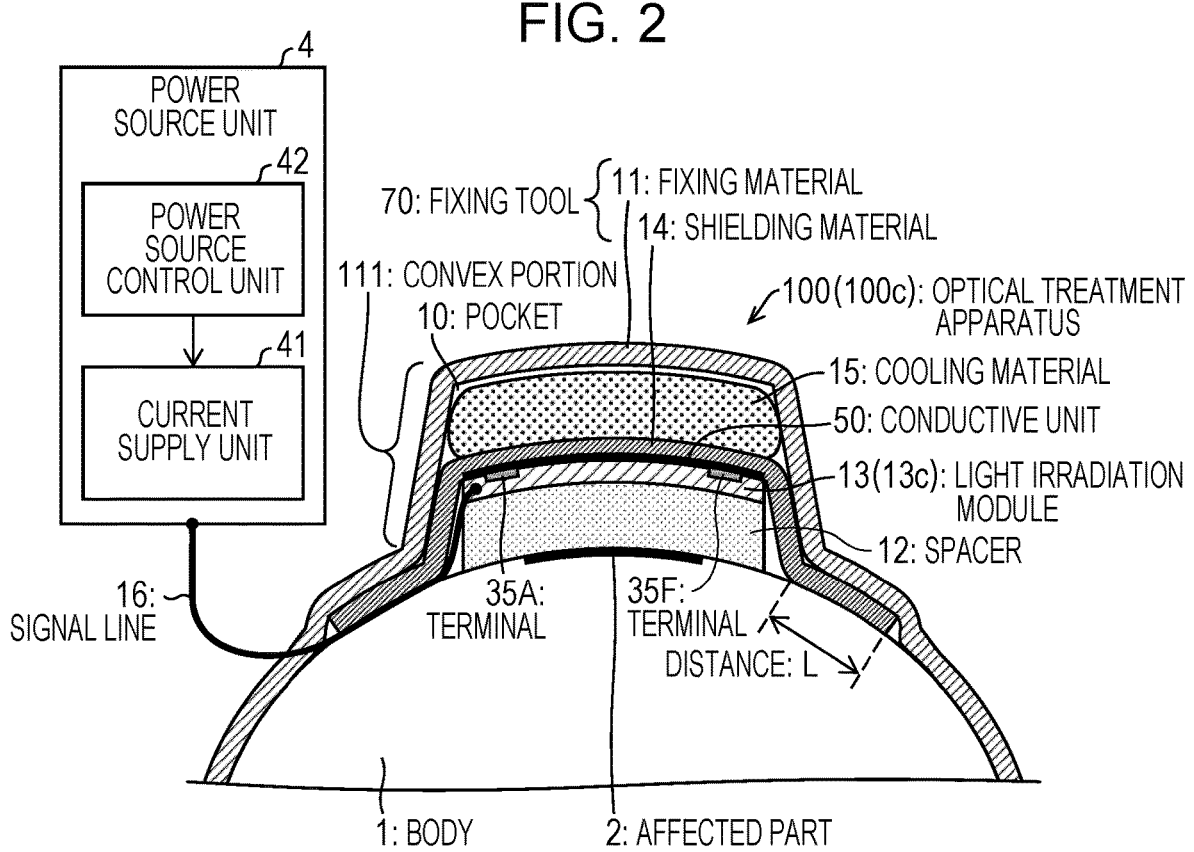
FIG. 2 is a schematic structural view illustrating the state where the optical treatment apparatus is mounted on the body.
Figure 3:
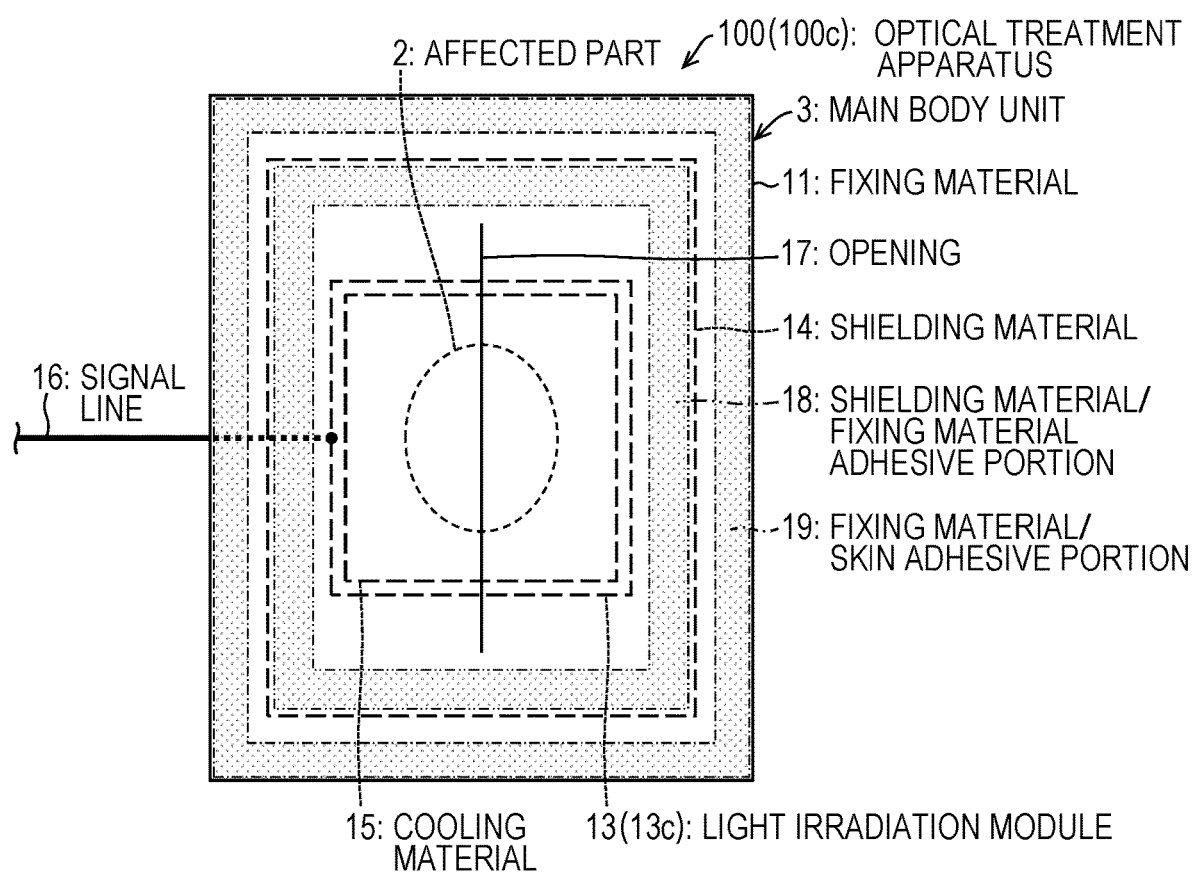
FIG. 3 is a plan view illustrating the state where the optical treatment apparatus is mounted on the body.

Embodiment 1 of the invention will be described with reference to FIGS. 1 to 6. Note that, the embodiment of the invention will be described by using a case where light irradiation therapy with a light irradiation module is performed for skin disease having a relatively small area as an example. FIG. 1 is a bird's eye view illustrating a state where an optical treatment apparatus 100 according to Embodiment 1 is mounted on a body, and more specifically is a bird's eye view illustrating a state where the optical treatment apparatus 100 is mounted on the body to treat an affected part 2 developed in the body 1, such as a hand, a foot, or a face. FIG. 2 is a schematic structural view illustrating the state where the optical treatment apparatus 100 is mounted on the body, and more specifically is obtained by adding a functional block of a power source unit 4 to a sectional view taken along a line A-A in FIG. 1. FIG. 3 is a plan view illustrating the state where the optical treatment apparatus 100 is mounted on the body.

The optical treatment apparatus 100 includes the power source unit 4, a main body unit (fixing tool) 3, and a signal line 16 that connects the power source unit 4 and the main body unit 3 as illustrated in FIGS. 1 to 3.

(Main Body Unit)

The main body unit 3 (fixing tool) includes a fixing material 11, a spacer 12, a light irradiation module 13, a shielding material 14, and a cooling material 15.

(Light Irradiation Module)

The light irradiation module 13 covers the affected part 2 and irradiates the affected part 2 with light when current is supplied from the power source unit 4.

Figure 4:
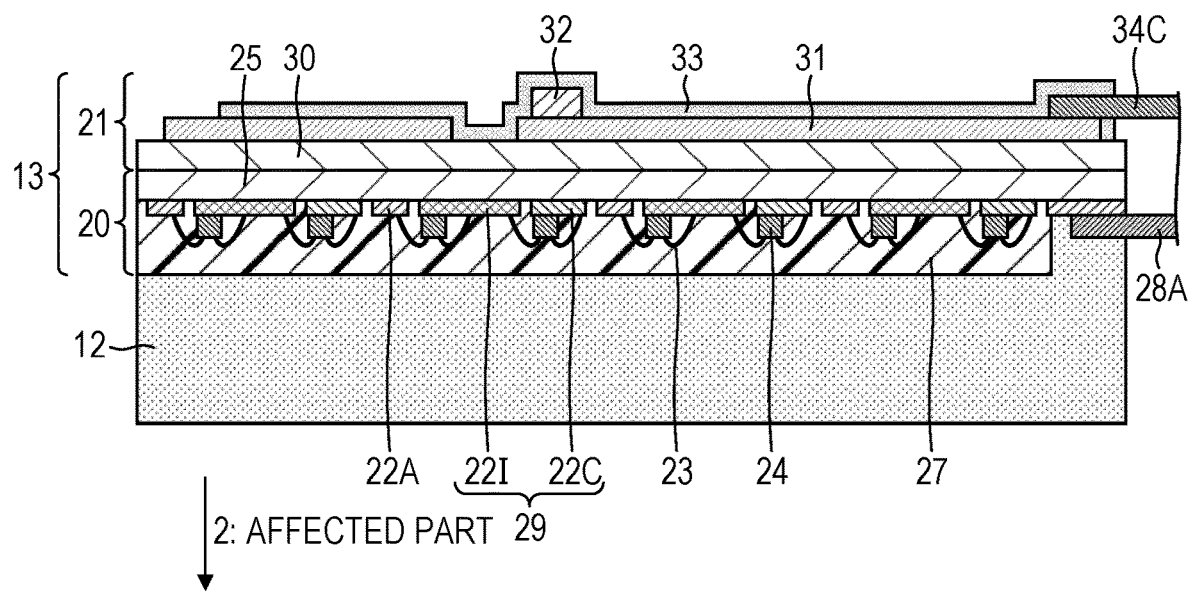
FIG. 4 is a sectional view of a light irradiation module of the optical treatment apparatus.
Figure 5:
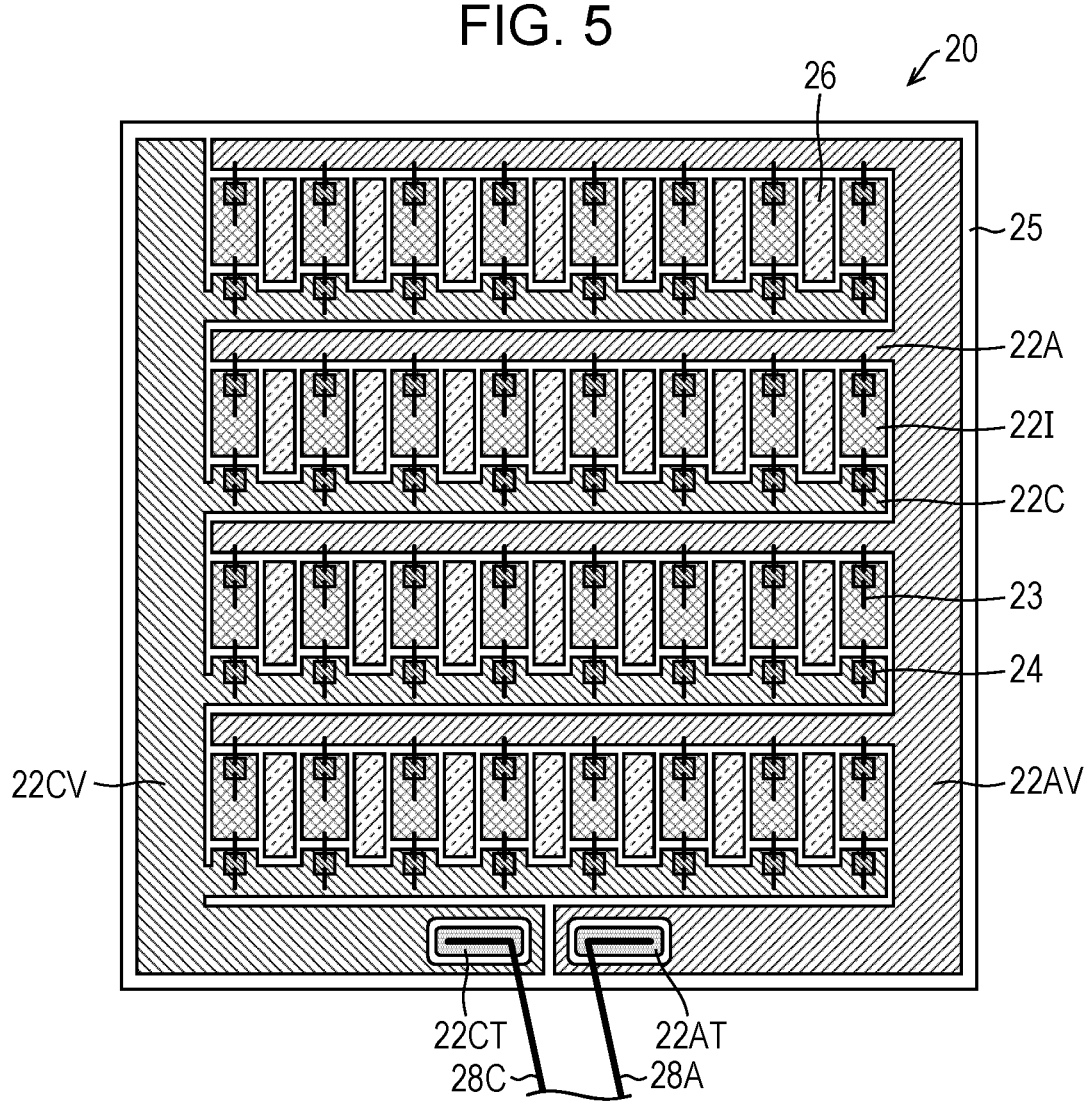
FIG. 5 is a plan view of a light emitting unit of the light irradiation module.
Figure 6:
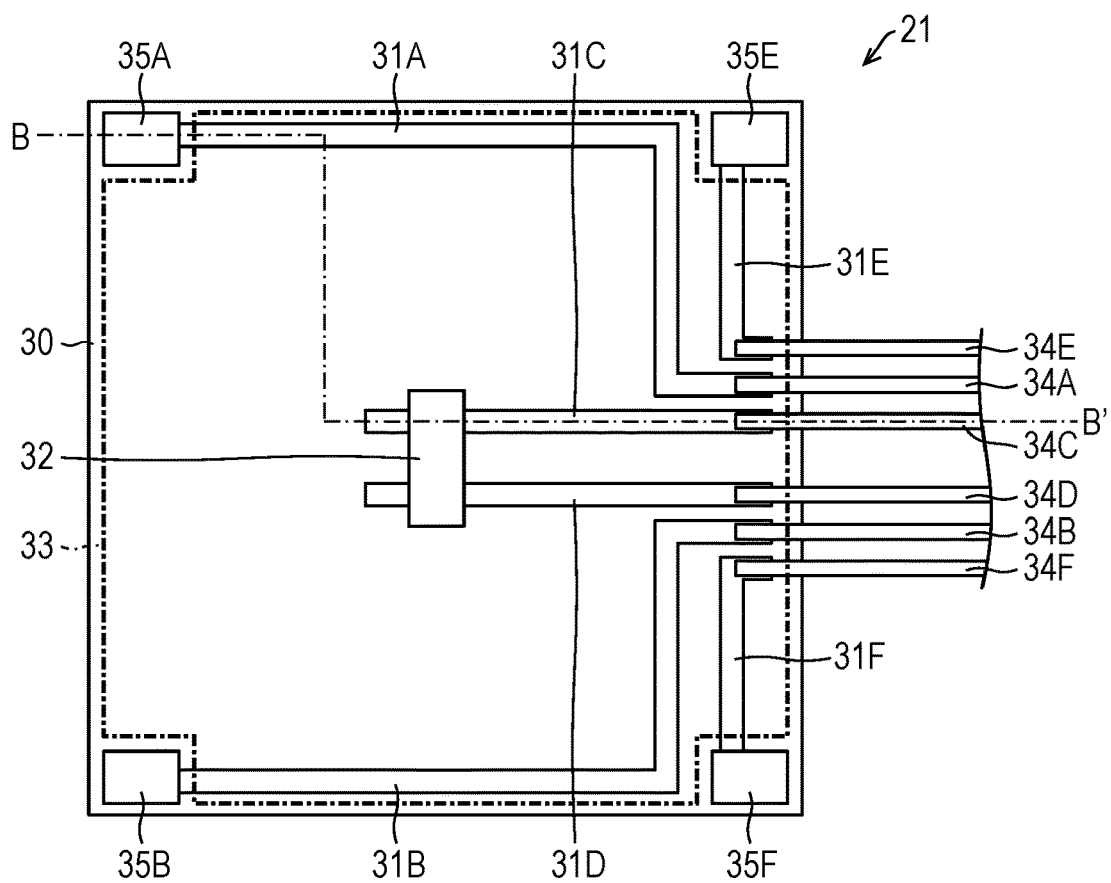
FIG. 6 is a plan view of a sensor unit of the light irradiation module.

With reference to FIGS. 4 to 6, the light irradiation module 13 will be described in detail below. FIG. 4 is a sectional view of the light irradiation module 13 of the optical treatment apparatus 100. Specifically, FIG. 4 is a sectional view taken along a line B-B' in FIG. 6. FIG. 5 is a plan view of a light emitting unit 20 of the light irradiation module 13. FIG. 6 is a plan view of a sensor unit 21 of the light irradiation module 13.

The light irradiation module 13 is connected to the power source unit 4 via the signal line 16, is supplied with predetermined current from the power source unit 4, and radiates light to the affected part 2 (target).

The light irradiation module 13 is assumed to include, for example, a substrate (flexible light irradiation substrate) in which an LED (Light Emitting Diode) that emits a predetermined wavelength spectrum is mounted on a resin surface having flexibility so as to enable lighting. A predetermined light emitting spectrum may be emitted by using an LED, which emits ultraviolet light, near-ultraviolet light, blue light, and the like, and a phosphor in combination. Moreover, in combination with light for treatment, specific medicine has been normally applied to the affected part 2 or taken in advance in many cases. It is assumed that an appropriate distance is kept between the LED and the affected part 2 to uniformly perform light irradiation for the affected part 2. However, medicine, a light wavelength which is used for treatment, details of the flexible light irradiation substrate, or the like does not affect the present embodiment and is thus not described in detail here.

(Details of Configuration of Light Irradiation Module)

The light irradiation module 13 includes the light emitting unit 20 and the sensor unit 21 as illustrated in FIG. 4. The light emitting unit 20 and the sensor unit 21 are stacked. Note that, the light emitting unit 20 and the sensor unit 21 are stacked so that a direction of an anode external connection unit 28A and a cathode external connection unit 28C in FIG. 5 is the same as a direction of a sensor output 34A to a sensor output 34F in FIG. 6.

(Light Emitting Unit)

As illustrated in FIGS. 4 and 5, the light emitting unit 20 is provided on the affected part 2 side (opposite to the shielding material 14 side) of the light irradiation module 13 and includes LED chips 24, a first flexible substrate 25, and a first protection film 27.

The first flexible substrate 25 is provided with, on a light emitting surface (surface on the side opposite to that of the sensor unit 21, front surface), a first wire layer 29 that includes anode wires 22A, cathode wires 22C, inter-chip wires 22I, an anode vertical wire 22AV, a cathode vertical wire 22CV, an anode terminal 22AT, a cathode terminal 22CT, and the like, and the LED chips 24 serving as light sources are arranged thereon in an array.

Specifically, as illustrated in FIG. 5, the first flexible substrate 25 has a square shape and the anode terminal 22AT and the cathode terminal 22CT are provided side by side along one side of the first flexible substrate 25.

From the anode terminal 22AT, an anode wire 22A extends along the one side toward a direction opposite to that of the cathode terminal 22CT, and is connected to the anode vertical wire 22AV that extends along a side adjacent to the one side. Further, from the anode vertical wire 22AV, the anode wires 22A are arranged at regular intervals in a direction parallel to the one side, and the LED chips 24 are connected to the wires at regular intervals.

Similarly to the anode wire 22A, from the cathode terminal 22CT, a cathode wire 22C also extends along the one side toward a direction opposite to that of the anode terminal 22AT and is connected to the cathode vertical wire 22CV that extends along a side adjacent to the one side. Further, from the cathode vertical wire 22CV, the cathode wires 22C are arranged at regular intervals in a direction parallel to the one side, and the LED chips 24 are connected to the wires at regular intervals.

An LED chip 24 connected to the anode wire 22A and an LED chip 24 connected to the cathode wire 22C are arranged facing each other and an inter-chip wire 22I is wired therebetween. A dummy pattern 26 is arranged between adjacent inter-chip wires 22I.

The LED chips 24 are arranged on wires and connected to the respective wires by bonding wires 23.

Various light emitting elements such as ultraviolet, blue-violet, blue, green, red, and infrared light emitting elements are selectable as the LED chips 24 in accordance with a therapeutic purpose. Though an example of wire bonding connection is described in FIG. 5, the LED chips 24 and the respective wires may be connected by flip chip connection, and in a case where each of the LED chips 24 has a vertical electrode structure, one terminal (normally, negative electrode) is connected to a wire by conductive paste and the other terminal is connected by wire bonding.

As a light emitting element, an LED device in which LED chips are stored in a package may be used in place of the LED chips 24 themselves. In a case where the LED device is used for the light emitting unit 20, mechanical strength is able to be increased, but it is required to consider that costs significantly increase and flexibility of the light emitting unit 20 is lowered.

The anode wires 22A and the cathode wires 22C are connected to the anode external connection unit 28A and the cathode external connection unit 28C at the anode terminal 22AT and the cathode terminal 22CT, respectively, and connected to the power source unit 4 via the signal line 16. For example, a lead wire is able to be used as the cathode external connection unit 28C and the anode external connection unit 28A.

The first protection film 27 covers and protects the respective wires, the LED chips 24, and connected parts thereof. The first protection film 27 is preferably made from a resin material, such as silicone resin, which is transparent or has a light-transmitting property and an excellent moisture proofing property. In a case where a phosphor is used to adjust a wavelength spectrum, the first protection film 27 itself is able to include the phosphor. A phosphor layer in which a phosphor and transparent resin are kneaded may be arranged on the first protection film 27.

The first flexible substrate 25 may be made from an insulating material having flexibility. For example, it is possible that the first flexible substrate 25 is a polyimide film and wires are made by etching copper foil and silver electroplating. A material of the respective wires preferably has low resistance and high reflectance of a front surface.

(Sensor Unit)

As illustrated in zips 4 and 6, the sensor unit 21 is provided on the shielding material 14 side of the light irradiation module 13 and further includes terminals 35A, 35B, 35E, and 35F, a thermistor 32, a second flexible substrate 30, and a second protection film 33 that are provided on a surface of the light irradiation module 13, which is on the shielding material 14 side.

The second flexible substrate 30 is a substrate that has an insulating flexible property and a square shape. At four corners of a surface (back surface) of the second flexible substrate 30, which is on the side opposite to that of the light emitting unit 20, the terminals 35A, 35B, 35E, and 35F are installed. The terminal 35A and the terminal 35F are installed at positions facing each other with a center of the second flexible substrate 30 therebetween and the terminal 35B and the terminal 35E are installed at positions facing each other with the center of the second flexible substrate 30 therebetween. The terminals 35A, 35B, 35E, and 35F are respectively connected to second wires 31A, 31B, 31E, and 31F.

The thermistor 32 (temperature sensor) detects temperature of the light irradiation module 13 and outputs information of the temperature to the power source unit 4 via sensor outputs 34C and 34D. The thermistor 32 is installed at a center part of the same surface of the second flexible substrate 30. The thermistor 32 is connected to second wires 31C and 31D.

The second wire 31A to the second wire 31F are also connected to a sensor output 34A to a sensor output 34F that transmit art electric signal to outside. The sensor output 34A to the sensor output 34F serve as a part of the signal line 16 and are connected to the power source unit 4.

In other words, on a surface of the sensor unit 21, which is on the side opposite to that of the light emitting unit 20, a second wire layer 31 is formed to be the terminals 35A, 35B, 35E, and 35F, and the second wire 31A to the second wire 31F, and the thermistor 32 is on the second wire layer 31.

A material of the second flexible substrate 30 may be any material as long as being an insulating flexible sheet and allowing formation of a wire on a whole surface thereof. As the second flexible substrate 30, a resin film, such as polyimide, polypropylene, or polyethylene, paper, or the like is usable.

Any material is usable for the second wire 31A to the second wire 31F as long as being a wire material that is able to be formed on the second flexible substrate 30. Though a material obtained by attaching copper foil or the like to a sheet and performing pattern processing for the resultant is also usable, a material that is able to be formed by screen printing or ink-jet printing is preferable in terms of costs. As the second wire 31A to the second wire 31F, for example, solder paste, silver paste, or the like that allows screen printing is usable. In ink-jet printing, an ink material made from fine particles of copper, silver, gold, or the like is usable.

The second protection film 33 is a protection film that has an insulating property and covers an almost entire surface of the second flexible substrate 30, which is on the side opposite to that of the light emitting unit 20. The terminals 35A, 35B, 35E, and 35F are not covered with the second protection film 33 and are exposed. Any material is usable as the second protection film 33 as long as being an insulating flexible material. A resin material, such as silicone, may coat the second flexible substrate 30, or a resin sheet, such as polyethylene, whose shape is processed in advance may be attached onto the second flexible substrate 30. Note that, in FIGS. 6, 7, 8, and 9, for simplification of the figures, a range covered with the second protection film 33 is indicated by a one-dot chain line.

To summarize the light irradiation module 13, the LED chips 24 serving as light sources are arranged in an array on a light emitting surface (front surface) of the first flexible substrate 25, the anode wires 22A and the cathode wires 22C serve as a part of the signal line 16 via the anode external connection unit 28A and the cathode external connection unit 28C and are connected to the power source unit 4 (the foregoing is the light emitting unit 20).

On the other hand, on the surface of the second flexible substrate 30, which is on the side opposite to that of the light emitting unit 20, the second wire 31A to the second wire 31F are provided, the thermistor 32 is connected between the second wire 31C and the second wire 31D, and the terminals 35A, 35B, 35E, and 35F are respectively provided at one ends of the second wires 31A, 31B, 31E, and 31F. The sensor output 34A to the sensor output 34F are connected to the other ends of the second wire 31A to the second wire 31F. The second protection film 33 that has an insulating property covers the entire surface of the second flexible substrate 30, which is on the side opposite to that of the light emitting unit 20, other than the terminals 35A, 35B, 35E, and 35F (the foregoing is the sensor unit 21).

In the present embodiment, in the light irradiation module 13, the light emitting unit 20 and the sensor unit 21 are formed on separate flexible substrates, and the resultants are attached to be integrated. In such a configuration, since the sensor unit 21 and the light emitting unit 20 are formed separately and bonded with each other, there is advantage that a step of applying thermal processing or large mechanical force to the light emitting unit 20 is not provided and the light emitting unit 20 is not adversely affected so that overall yield is able to be improved. For example, in a case where the first wire layer 29 of the light emitting unit 20 is provided only on the front surface of the first flexible substrate 25 as illustrated in FIG. 5, after the LED chips 24 are mounted and the first protection film 27 is formed, the light emitting unit 20 does not pass through a step other than the step of being attached to the sensor unit 21, so that there is almost no factor of reduction of the yield.

Moreover, on a back surface (surface on the side opposite to the affected part 2 side) of the first flexible substrate 25, the thermistor 32 may be mounted and the second wire layer 31 and the second protection film 33 may be formed. In this case, a step of mounting the thermistor 32 and forming the second wire layer 31 and the second protection film 33 may damage the LED chips 24 or connected parts between the LED chips 24 and the respective wires.

The light irradiation module 13 may be configured so that wires of the light emitting unit 20 are provided on the back surface (surface on the sensor unit 21 side) of the first flexible substrate 25. This makes it possible to arrange the LED chips 24 up to an end of the first flexible substrate 25 and is thus effective when an area of light emission is increased, or the number of parallel wires is increased to reduce an operating voltage. In a case where the sensor unit 21 is directly formed on the light emitting unit 20 that has wires on both surfaces of the first flexible substrate 25, it is necessary that, after the first protection film 27 is formed on the first wire layer 29 formed on the back surface, the second wire 31A to the second wire 31F are further provided, terminals of the sensor output 34A to the sensor output 34F are connected, and the second protection film 33 is provided.

Though it is advantageous to separately form the light emitting unit 20 and the sensor unit 21 in terms of production yield, there is also a factor of an increase in costs, for example, that the second flexible substrate 30 is required and the step of attaching the sensor unit 21 and the light emitting unit 20 is added. As long as reduction in the yield is able to be suppressed while sufficiently protecting the front surface (affected part 2 side) of the light emitting unit 20, it is also possible that the second wire layer 31, and the terminals 35A, 35B, 35E, and 35F that are exposed are formed on the back surface (surface on the side opposite to the affected part 2 side) of the first flexible substrate 25 and a sensor part such as the thermistor 32 is mounted. The sensor unit 21 is also able to be formed by being directly attached to a back side of the light emitting unit 20 within an allowable range of whole costs.

Note that, for example, in a case where there is no possibility of a temperature rise because the cooling material 15 is installed or a case where a patient himself or herself is able to immediately remove the fixing material 11 described below upon heating, the thermistor 32 is also able to be omitted from a viewpoint of cost reduction.

The light irradiation module 13 having higher light emission efficiency generates less amount of heat and is thus preferable.

(Spacer)

The spacer 12 (transparent spacer) is a transparent spacer that is positioned between the light irradiation module 13 and the affected part 2 and keeps a distance between the affected part 2 and the light irradiation module 13 constant.

The spacer 12 is arranged between the affected part 2 and the light irradiation module, achieves uniform light irradiation, and functions as a heat insulator that achieves uniform light irradiation and does not allow heat generated by the light irradiation module 13 to be directly transferred to the affected part 2. Thus, the heat from the light irradiation module 13 is able to be prevented from being directly transferred to the affected part 2. Since the spacer 12 is able to prevent the heat from the light irradiation module 13 from being directly transferred to the affected part 2, a temperature rise of the light irradiation module 13 is able to be permitted to a certain degree, so that a large-sized cooling device is not required. Furthermore, in the optical treatment apparatus 100, treatment is finished in a relatively short time, so that a cooling water circulation device or the like does not need to be installed and the patient is able to be prevented from being restrained during the treatment.

The spacer 12 has transparency with respect to therapeutic light. In other words, the spacer 12 transmits therapeutic light.

The spacer 12 preferably has a plate shape that has a constant thickness and is constituted by a flexible and transparent material. For example, the spacer 12 is preferably made from a resin material such as styrene elastomer, urethane rubber, or silicone rubber. Since the LED chips 24 are arranged in an array in the light emitting unit 20, a distance between the affected part 2 and the spacer 12 needs to be kept constant so that the affected part 2 receives uniform light irradiation. The spacer 12 also has a function as a heat insulator for preventing the affected part 2 from feeling cold when the cooling material 15 is used.

As the thickness of the spacer 12 increases, more uniformized light irradiation and a higher heat insulating effect are achieved, however, as the thickness of the spacer 12 increases, it becomes difficult for the spacer 12 to be deformed so as to conform to the affected part 2. Thus, in such a trade-off relationship, an optimum value of the thickness of the spacer 12 needs to be selected. When a curvature of a typical human body is considered, a suitable thickness of the spacer 12 is about 2 mm to 10 mm, and a most suitable thickness thereof is about 3 mm to 7 mm. The spacer 12 of a plate shape is difficult to be fitted around a finger, a tip of a nose, or the like and preferably has another form according to a form of the affected part.

Since the spacer 12 and the light irradiation module 13 have almost the same sizes and are arranged so that centers thereof almost overlap with each other, only the light irradiation module 13 is illustrated in FIGS. 1 and 3. The spacer 12 that is slightly greater than the light irradiation module 13 is easily positioned when being placed on the affected part 2. However, even when (1) the spacer 12 and the light irradiation module 13 have completely the same size, (2) the spacer 12 is smaller than the light irradiation module 13, or (3) the center of the spacer 12 and the center of the light irradiation module 13 are deviated, there is no problem of use as long as the spacer 12 covers the first protection film 27.

(Shielding Material)

The shielding material 14 (light shielding unit) covers the affected part 2 and the light irradiation module 13.

Specifically, the shielding material 14 is positioned on the side of the light irradiation module 13, which is opposite to the side of the affected part 2, in a state where the optical treatment apparatus 100 is mounted on the patient, and covers the light irradiation module 13 to shield light, radiated to the affected part 2 by the light irradiation module 13, leaking to a part other than the affected part 2.

In particular, out of the light radiated by the light irradiation module 13, light emission from a side surface of the spacer 12 constitutes a main part of the light directed to the part other than the affected part 2. Since the spacer 12 has a transparent property, light is also emitted from the side surface. Thus, the shielding material 14 needs to cover the side surface of the spacer 12. The shielding material 14 preferably covers also a boundary part between the light irradiation module 13 and the spacer 12 and a back surface of the light irradiation module 13, from each of which light may be leaked. When the first flexible substrate 25 that constitutes the light irradiation module 13 does not have a transparent property, no leakage of light occurs from the back surface.

The shielding material 14 is arranged between the light irradiation module 13 and the fixing material 11 described below and completely covers the light irradiation module 13 and the spacer 12, thus making it possible to reduce leakage of the light to the part other than the affected part 2 to an almost negligible degree.

The shielding material 14 includes a conductive unit 50 that is provided at a position facing the terminals 35A, 35B, 35E, and 35F on the surface of the shielding material 14, which is on the light irradiation module 13 side, in a state where the optical treatment apparatus 100 is mounted on the patient.

The shielding material 14 is fixed, at an outer periphery thereof, to the fixing material 11 by means of adhesion or the like with use of an adhesive agent. This corresponds to a shielding material/fixing material adhesive portion 18 illustrated in FIG. 3. Thereby, it is possible to save labor for separately placing the shielding material 14. However, the affected part 2 is able to be treated even when the shielding material 14 does not necessarily adhere to the fixing material 11.

Only covering ends of the light irradiation module 13 and the spacer 12 by the shielding material 14 is insufficient to completely shield light leaked from the ends of the light irradiation module 13 and the spacer 12, and skin (body 1) on further outside of the ends needs to be covered with the shielding material 14.

In normal adhesion to skin, there is a case where a gap is generated between the shielding material 14 which covers the signal line 16 and the signal line 16 or a case where wrinkles are generated in the shielding material 14, so that light partially leaks in a horizontal direction. To prevent such a case, a distance L (refer to FIG. 2) from the end of the light irradiation module 13 or the spacer 12 to an end of the shielding material 14 needs to be sufficiently long.

By thoroughly eliminating be wrinkles or the gap, great leakage of light is able to be prevented as long as the distance L is at least 5 mm. Thus, the shielding material 14 desirably extends to an outer side by at least 5 mm or more from an outer edge of the light irradiation module 13 or the spacer 12 in a state of receiving pressure (state of being fixed) by the fixing material 11. To save labor for eliminating the wrinkles or the gap, the distance L needs to be 10 mm or more, and is preferably 15 mm or more. Since the distance L is a distance on one side from the end of the light irradiation module 13 to the end of the shielding material 14, the aforementioned numeral is doubled when a width of the shielding material 14 and a width of the light irradiation module 13 are compared.

The shielding material 14 is most preferably made from aluminum foil having a thickness of 50 μm to 200 μm, but may be made from a composite material in which a resin film is stacked on thin aluminum foil (having a thickness of about 25 μm). Additionally, the shielding material 14 may be made from a composite material in which a gold thin film is formed on copper foil or a resin film, or metal foil in which a gold thin film is provided on a surface of aluminum foil. In such a case, the shielding material 14 itself constitutes the conductive unit 50.

Only in a part of the shielding material 14, which faces the light irradiation module 13, for example, a gold thin film, a copper thin film, an aluminum thin film, or the like may be arranged as the conductive unit 50 on a light-shielding film that has an insulating property. The shielding material 14 does not need to have the conductive unit 50 over the entire surface thereof on the light irradiation module 13 side and may be provided with the conductive unit 50 only in an area connecting terminals (for example, the terminal 35A and the terminal 35F) between which conduction is checked.

The conductive unit 50 is only required to be provided on at least one surface of the shielding material 14 and the conductive unit 50 is only required to be arranged at a position facing the terminals 35A, 35B, 35E, and 35F in the state where the optical treatment apparatus 100 is mounted on the patient. That is, in a case where the shielding material 14 has a composite material or metal foil which has a gold thin film, a gold thin film surface is arranged on the light irradiation module 13 side. The gold thin film surface is preferable because contact conductivity is scarcely decreased by suffering from surface oxidation. However, use of aluminum foil is more advantageous than use of gold in terms of costs.

In a case where contact of a terminal of the sensor unit 21 and the conductive unit 50 is poor, for example, by rubbing a surface of aluminum foil of the conductive unit 50 of the shielding material 14 with paper, cloth, or the like to make tiny scratches on the surface before the shielding material 14 is placed on the light irradiation module 13, electrical contact is able to be secured.

(Fixing Material)

The fixing material 11 (fixing material) fixes the light irradiation module 13 and the spacer 12 at positions where the affected part 2 is covered. The fixing material 11 applies, via the shielding material 14, predetermined pressure so as to press the light irradiation module 13 against the spacer 12 and fixes the light irradiation module 13 and the spacer 12 at installation positions. Here, the Predetermined pressure means pressure by which the light irradiation module 13 and the spacer 12 are fixed so as not to be removed from the affected part 2, conduction between the terminals 35A, 35B, 35E, and 35F and the conductive unit 50 is secured, and the patient does not feel pain in the affected part 2.

Specifically, as illustrated in FIGS. 1 and 2, the fixing material 11 keeps the light irradiation module 13 and the spacer 12 at positions where the affected part 2 is irradiated with light, in a state where the light irradiation module 13 and the spacer 12, which are between the affected part 2 and the shielding material 14, and the shielding material 14 are overlapped. In other words, the fixing material 11 fixes the positions of the light irradiation module 13 for phototherapy and the spacer 12 with respect to the body 1. The shielding material 14 that includes the conductive unit 50 is arranged between the fixing material 11 and the light irradiation nodule 13. Before the optical treatment apparatus 100 is mounted, the light irradiation module 13 and the fixing material 11 are not fixed and are able to be separated. When the optical treatment apparatus 100 is mounted, the predetermined pressure is applied to the light irradiation module 13 and the spacer 12 by the fixing material 11 and the light irradiation module 13 and the spacer 12 are fixed at the positions where the affected part 2 is covered.

Since the light irradiation module 13 and the fixing material 11 are able to be separated, the optical treatment apparatus 100 does not need to be prepared for each size of the affected part 2 and only the light irradiation module 13 is able to be replaced in accordance with a size of the affected part 2.

To perform light shielding as reliable as possible, the fixing material 11 preferably has a size completely covering at least the shielding material 14, but is not necessarily required to completely cover the shielding material 14 as long as effective light shielding is enabled.

The fixing material 11 may be a sheet that has flexibility and is constituted by cloth, leather, nonwoven fabric, a resin film, rubber, artificial leather, synthetic leather, metal foil, paper, or the like, or a composite material thereof.

The fixing material 11 has an elastic property and has a flat sheet shape before being mounted on the affected part 2. The spieling material 14 adheres to the fixing material 11 in advance by the shielding material/fixing material adhesive portion 18 and a pocket 10 (space) is formed between the fixing material 11 and the shielding material 14. An opening 17 is provided in the fixing material 11 at a position corresponding to the pocket 10. After the fixing material 11 is mounted on the patient, the cooling material 15 or the like is able to be inserted into the pocket 10 through the opening 17. The opening 17 preferably has an open/close mechanism that is openable or closable by a fastener or the like to prevent the cooling material 15 from being dropped out.

The fixing material 11 has, at an outer periphery of a surface thereof on the affected part 2 side, a fixing material/skin adhesive portion 19 (refer to FIG. 3) that fixes the fixing material 11 to the body.

When the fixing material 11 is mounted on the body 1, first, in a state where the spacer 12 and the light irradiation module 13 are positioned between the shielding material 14 and the body 1, both ends of the fixing material 11 are pulled, and the spacer 12 and the light irradiation module 13 are pressed against the body 1 via the shielding material 14. Further, in a state where the spacer 12 and the light irradiation module 13 are pressed against the body 1 (in a state where the predetermined pressure is applied to the spacer 12 and the light irradiation module 13 via the shielding material 14 toward the body 1), the fixing material 11 is fixed to the body 1 by the fixing material/skin adhesive portion 19. Thereby, the fixing material 11 is able to fix positions of the spacer 12, the light irradiation module 13, and the shielding material 14 with respect to the body 1. Next, the cooling material 15 that is cooled in advance is inserted into the pocket 10 through the opening 17.

After an attaching work of the fixing material 11, the fixing material 11 is deformed, due to the elastic property thereof, so as to have a convex portion 111 that protrudes to a side opposite to that of the affected part 2 and the pocket 10 is bulged. Moreover, with the elastic property, the shielding material 14 is pressed against the light irradiation module 13 via the cooling material 15.

(Cooling Material)

The cooling material 15 cools the light irradiation module 13.

In a case where the light irradiation module 13 generates great heat and may have temperature of 42° C. or more within a predetermined treatment time, cooling is required. When the cooling material 15 that is cooled (for example, from about 0° C. to 15° C.) in advance is inserted into the pocket 10 to cool the light irradiation module 13, a temperature rise of the light irradiation module 13 is able to be suppressed. In the optical treatment apparatus 100, treatment is performed in a relatively short time, so that a large-sized cooling device that is required in long-time treatment and circulates water becomes unnecessary. Since the shielding material 14, the light irradiation module 13, and the spacer 12 are between the cooling material 15 and the body 1, the cooling material 15 does not directly contact the body 1 and the patient does not feel very cold.

As the cooling material 15, a gel material that is generally used and made from sodium polyacrylate and water is preferably used in terms of costs. A bag in which water is simply enclosed is also usable as the cooling material 15. For example, water that is cooled to 10° C. or less in a normal refrigerator or the like is usable as the cooling material 15. Water at 0° C. or less is also usable as the cooling material 15.

In addition, an instantaneous cooling material that is made from water and urea/ammonium nitrate or the like is also usable as the cooling material 15. In the instantaneous cooling material, water and urea/ammonium nitrate are enclosed in different rooms, and when the resultant is hit from outside to break a wall between both of them, cooling is achieved by endothermic reaction caused by mixture, so that temperature is able to be reduced to 15° C. or less in about one minute.

(Power Source Unit and Signal Line)

The optical treatment apparatus 100 has an interlocking function of stopping supply of current in a case where the pressure applied by the fixing material 11 becomes lower than the predetermined pressure or a case where existence of the shielding material 14 is not able to be detected. In other words, in the optical treatment apparatus 100, the conductive unit 50 is used as a power source control sensor (sensor) and the power source unit 4 stops the supply of the current in response to a signal from the conductive unit 50.

Specifically, the optical treatment apparatus 100 includes the terminals 35A and 35F as at least one pair of electrodes that are provided at positions facing each other with the center of the light irradiation module 13 therebetween at an end of the surface of the light irradiation module 13, which is on the shielding material 14 side, and the conductive unit 50 that is provided at a position facing the light irradiation module 13 on the surface of the shielding material 14, which is on the light irradiation module 13 side, and the optical treatment apparatus 100 has the interlocking function of stopping the supply of the current to the light irradiation module 13 in a case where the terminal 35A and the terminal 35F are turned out to be nonconductive due to separation between conductive unit 50 and the light irradiation module 13 caused by pressure loss, where the pressure applied by the fixing material 11 becomes lower than the predetermined pressure.

The light irradiation module 13 includes the thermistor 32 and the optical treatment apparatus 100 has the interlocking function of stopping the supply of the current to the light irradiation module 13 in a case where an output of the thermistor 32 is higher than predetermined temperature.

The power source unit 4 will be described in detail below.

The power source unit 4 includes a current supply unit 41 and a power source control unit 42.

The current supply unit 41 supplies current to the light irradiation module 13.

The power source control unit 42 instructs the current supply unit 41 to supply or stop the current to the light irradiation module 13. The power source control unit 42 determines whether or not at least one pair of the terminal 35A and the terminal 35F is conductive, and when the terminal 35A and the terminal 35F are nonconductive, instructs the current supply unit 41 to stop the supply of the current.

Specifically, when the terminal 35A and the terminal 35F contact the conductive unit 50, for example, a closed circuit appears between the power source unit 4, the sensor output 34A, the second wire 31A, the terminal 35A, the terminal 35F, the second wire 31F, and the sensor output 34F. The power source control unit 42 supplies current from the sensor output 34A to the terminal 35A and detects an output from the sensor output 34F to thereby determine whether or not the terminal 35A and the terminal 35F are conductive.

When there is an output from the sensor output 34F, the power source control unit 42 determines that the terminal 35A and the terminal 35F are conductive and instructs the current supply unit 41 to supply the current to the light irradiation module 13. When there is no output from the sensor output 34F, the power source control unit 42 determines that the terminal 35A and the terminal 35F are nonconductive and instructs the current supply unit 41 to stop the current to the light irradiation module 13.

Thereby, for example, in a case where the shielding material 14 is not placed because of mistake during treatment and existence of the shielding material 14 is not detected, the terminal 35A and the terminal 35F are not connected via the conductive unit 50, so that the terminal 35A and the terminal 35F are nonconductive and current is not supplied to the light irradiation module 13. In other words, the light irradiation module 13 does not radiate light unless being covered with the shielding material 14. As a result, the patient or a medical practitioner is able to be prevented from seeing powerful light because the light irradiation module 13 is not covered with the shielding material 14.

In a case where, for example, the patient hits against something and the light irradiation module 13 is removed from the body 1, the terminals 35A and 35F are separated from the conductive unit 50 and become nonconductive, so that the current is immediately stopped. As a result, irradiation of light is able to be immediately stopped when the light irradiation module 13 is removed from the body 1, thus making it possible to prevent the patient or the medical practitioner from seeing powerful light. Note that, both of pressure loss by the fixing material 11 and lack of the shielding material 14 can be detected by conductivity between the terminal 35A and the terminal 35F.

Specifically, for example, when the terminal 35A and the terminal 35F are nonconductive, the power source unit 4 may determine that the pressure applied by the fixing material 11 becomes lower than the predetermined pressure, and when the terminal 35A and the terminal 35F are nonconductive, the power source unit 4 may determine that existence of the shielding material 14 is not detected.

The power source control unit 42 may control the current supply unit 41 so that the current supply unit 41 supplies the current to the light irradiation module 13, when both of the terminal 35A and the terminal 35F and the terminal 35B and the terminal 35E are conductive, and a combination of terminals (electrodes) that are paired is able to be freely set.

The current supply unit 41 supplies predetermine current to the light irradiation module 13 and causes the light irradiation module 13 to radiate light for a predetermined time. For example, in a case where current of 400 mA is supplied to the light irradiation module 13 illustrated in FIG. 5, in which 64 blue-violet light emitting diodes (peak wavelength: 405 nm) are arrayed in 8 rows and 8 columns with a pitch of 5 mm, driving voltage of about 7 V is required. The current of 12.5 mA flows through each of the LED chips 24 and light irradiation intensity of 37.5 mW/cm$^2$ is obtained near a center of the light irradiation module 13. In a case where a dose amount of energy required for treatment is 25 J/cm$^2$, irradiation is able to be completed in about eleven minutes. The irradiation time is assumed to be one hour or less at the longest, and treatment is normally completed in about several minutes to twenty minutes. Thus, power is not necessarily required to be obtained from an AC power source and a dry battery or a storage battery may be used as the power source.

In conclusion, the power source unit 4 preferably has a function of setting a required current amount and a required time in accordance with target treatment, a function of, in actual treatment, starting irradiation and stopping the irradiation after a predetermined time has lapsed, and first and second interlocking functions described below.

Specifically, the first interlocking is a function of supplying the current to the light irradiation module 13, for example, only in a case where the terminal 35A and the terminal 35F are conductive, and both of the terminal 35B and the terminal 35E are conductive. The first interlocking is able to be achieved when the power source control unit 42 controls the current supply unit 41 so as to supply the current to the light irradiation module 13 only in the case where both of the terminal 35A and the terminal 35F and the terminal 35B and the terminal 35E are conductive as described above. A combination of terminals to be conductive is able to be freely set and at least one pair of terminals may be set.

The second interlocking function is a function of stopping light irradiation of the light irradiation module 13 in a case where a temperature rise of the light irradiation module 13 is detected by an output of the thermistor 32. In a case where the light irradiation is performed in a short time, since a heat amount of about twice to five times of a dose amount of energy is generated, when the dose amount is large, the temperature of the light irradiation module 13 also rises greatly, so that a cooling means is essential. However, a case where the patient suffers from low temperature burnt due to mistake of forgetting to insert the cooling material 15 during treatment or a case where the cooling material 15 is dropped out because the patient moves around is also considered. The second interlocking function is preferably provided to avoid a problem due to a temperature rise of the light irradiation module 13 resulting from forgetting to insert the cooling material 15, loss of the cooling material 15 due to dropping thereof, or the like. That is, when the temperature indicated by the thermistor 32 becomes higher than predetermined temperature, the current supply from the power source unit 4 to the light irradiation module 13 is stopped, so that safety is secured.

The second interlocking is able to be achieved in a manner described below. That is, the power source control unit 42 acquires temperature information of the light irradiation module 13, which is output from the thermistor 32, and determines whether or not the output of the thermistor 32 is greater than predetermined temperature. The power source control unit 42 controls the current supply unit 41 to supply the current to the light irradiation module 13 when the output of the thermistor 32 is equal to or less than the predetermined temperature, and to stop the current supply to the light irradiation module 13 when the output of the thermistor 32 is greater than the predetermined temperature.

The signal line 16 integrally connects, as one cable, the anode external connection unit 28A and the cathode external connection unit 28C through which power is supplied to the light emitting unit 20, and the sensor output 34A to the sensor output 34F of the sensor unit 21 to the power source unit 4. Though the signal line 16 achieves connection between the power source unit 4 and the light irradiation module 13, the signal line 16 may not be one cable and a relatively short cable may be attached to the light irradiation module 13 so that the connection is achieved via a cable attached to the power source unit 4 side and a connector. In a case where the power source unit 4 is mounted on the body of the patient, the cable of the light irradiation module 13 side may be directly connected to the power source unit 4.

In recent years, with improvement of an LED serving as a light source and utilization of new medicine, new therapy by which single treatment is able to be finished in about several minutes by increasing light irradiation intensity to around 100 mW/cm$^2$ and a disposable flexible optical treatment apparatus that is used for a small affected part and is mounted on the affected part without necessity of restraining a patient have been developed, but the therapy and the optical treatment apparatus also have the following problems about (1) to (3). The problems include (1) safety countermeasure against leakage of light to outside during treatment due to a significant increase in light intensity, (2) preventive countermeasure against a temperature rise of an affected part, which does not restrain a patient, and (3) safety countermeasure against an abnormal case, for example, where an optical treatment apparatus is removed from an affected part when a patient acts freely during treatment. According to the present embodiment, the problems about (1) to (3) are also able to be solved.

Note that, as illustrated in FIG. 2, the fixing material 11 and the shielding material 14 are able to be treated as a fixing tool 70 separately from other configurations and the fixing tool 70 is able to be commercially traded alone.

Modified Example

Figure 7:
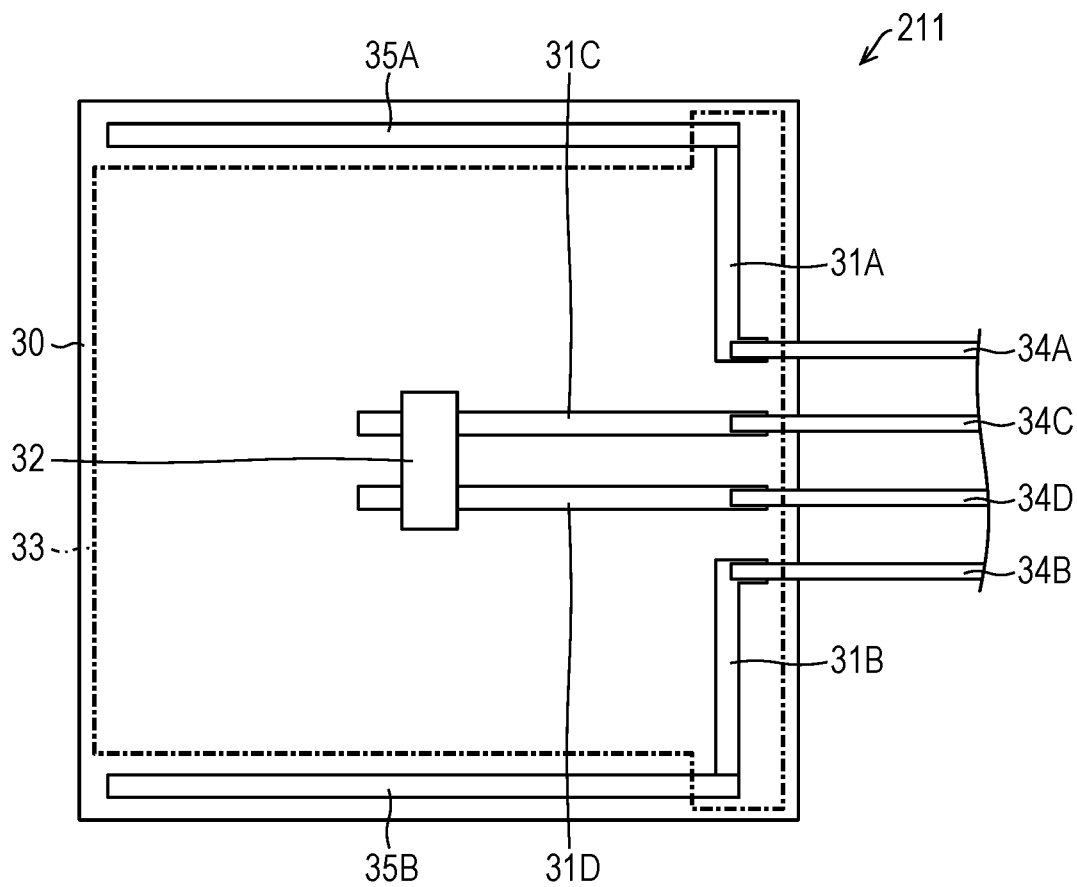
FIG. 7 is a plan view illustrating a modified example of the sensor unit of the light irradiation module.
Figure 8:
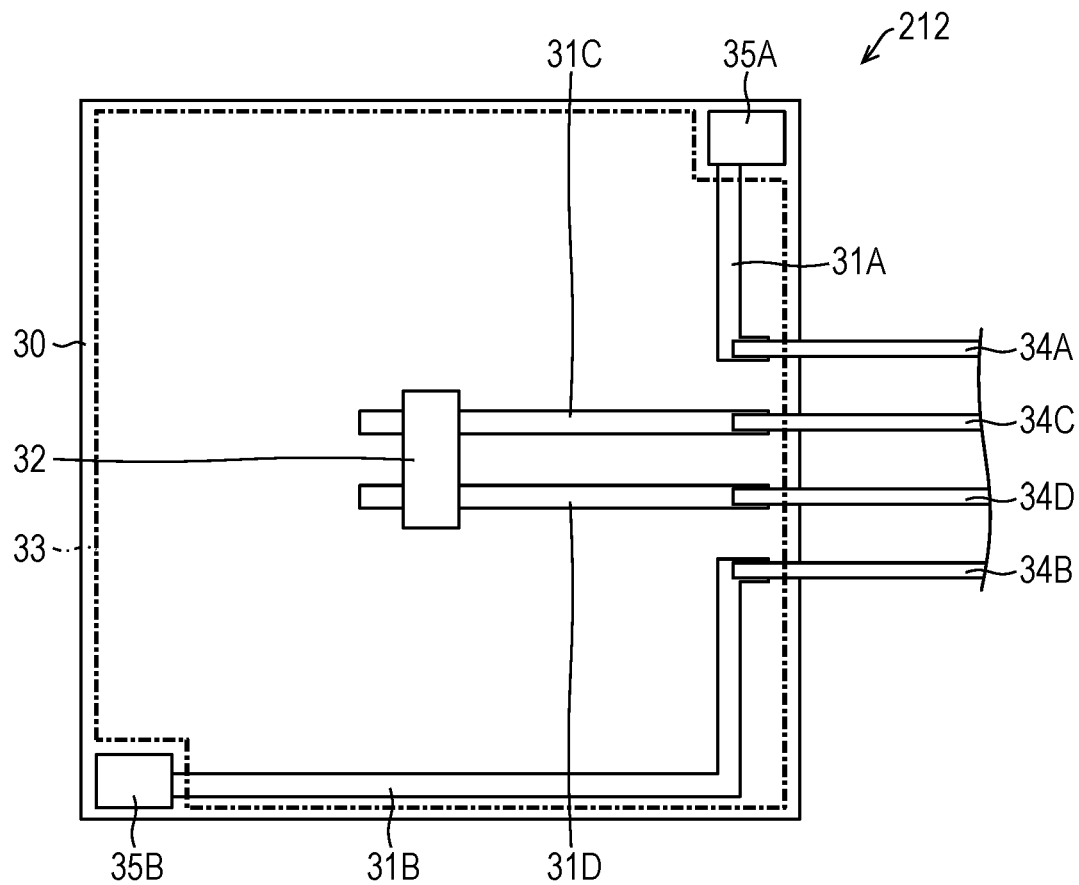
FIG. 8 is a plan view illustrating another modified example of the sensor unit of the light irradiation module.
Figure 9:
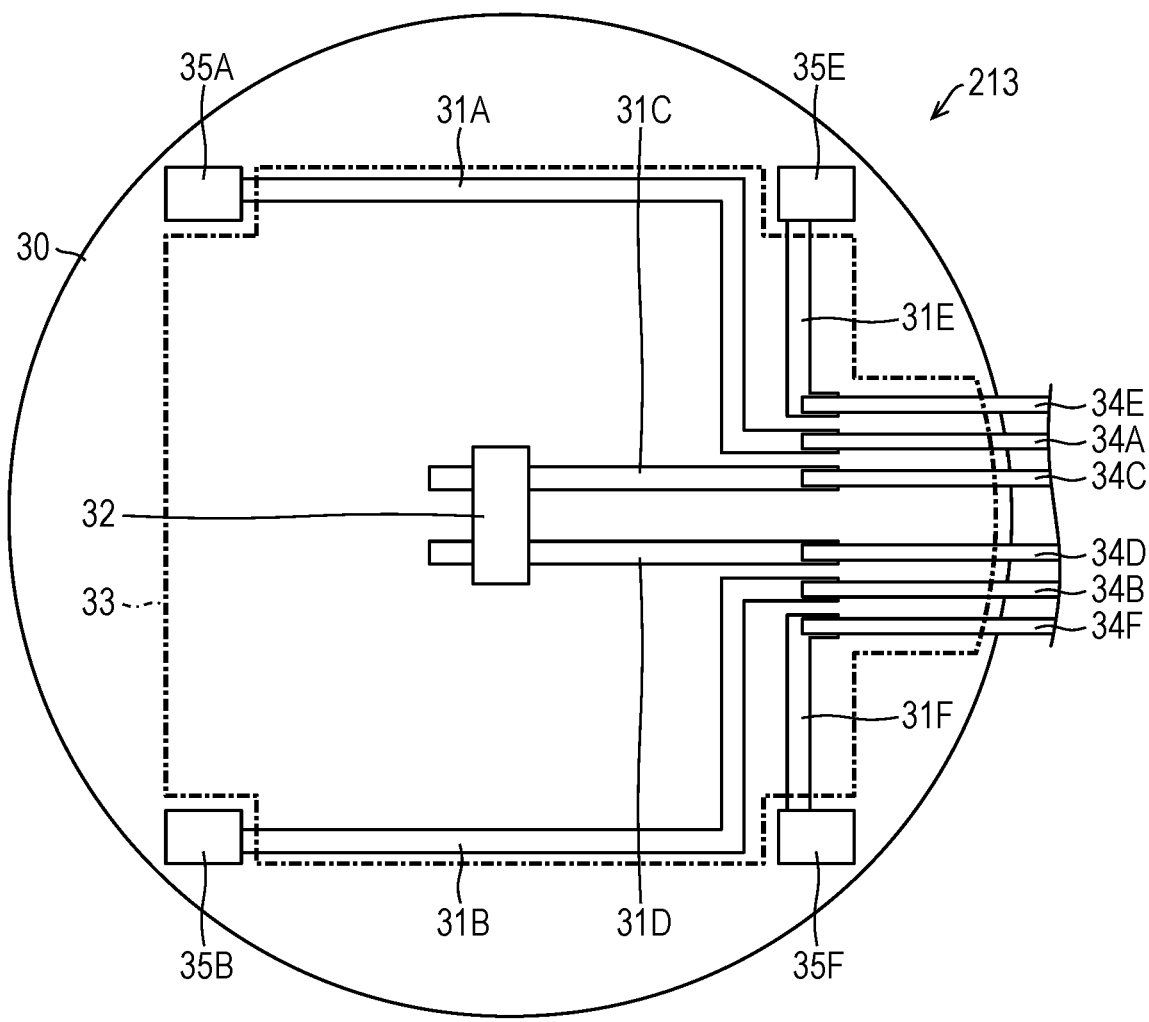
FIG. 9 is a plan view illustrating still another modified example of the sensor unit of the light irradiation module.

A modified example of Embodiment 1 of the invention will be described with reference to FIGS. 7 to 9. FIG. 7 is a plan view of a sensor unit 211 as a modified example of the sensor unit 21 of the light irradiation module 13. FIG. 8 is a plan view of a sensor unit 212 as another modified example of the sensor unit 21. FIG. 9 is a plan view of a sensor unit 213 as still another modified example of the sensor unit 21.

Though the terminals 35A, 35B, 35E, and 35F are provided in the sensor unit 21 in FIG. 6, the number thereof may not be always four. As in the sensor unit 211 illustrated in FIG. 7, the terminals 35A and 35B that are linear may be provided along facing sides of the second flexible substrate 30.

As in the sensor unit 212 illustrated in FIG. 8, the terminals 35A and 35B that have a dot shape may be provided at two diagonal points of the second flexible substrate 30. In the case of illustration of FIGS. 7 and 8, the terminals 35E and 35F, the sensor outputs 34E and 34F, and the second wires 31E and 31F are able to be omitted. In addition, only a combination of the terminal 35A and the terminal 35B in FIG. 6 may be provided. Note that, the dot shape includes an island shape and a rectangular shape.

The similar is also applied to a case where a shape of the second flexible substrate 30 has a circular shape or an elliptical shape as in the sensor unit 213 illustrated in FIG. 9, and the sensor unit 213 preferably includes at least one pair of terminals (terminals 35A and 35F or terminals 35B and 35E) facing with a center point of the light irradiation module 13 therebetween. The number of terminals may not be always four and the terminals may be one pair of terminals at symmetrical positions with respect to a center line passing through the center point of the light irradiation module 13.

In FIGS. 4 and 6, though the sensor unit 21 is constituted with the second flexible substrate 30 as a base, the second flexible substrate 30 is not essential. Since it is only required that at least one pair of terminals that is conductive when being covered with the shielding material 14 is provided, a similar function is able to be achieved only by fixing terminals, which are obtained by soldering a metal piece to a tip end of a lead wire, to a back surface of the light emitting unit 20 with an adhesive agent. The thermistor 32 may be also soldered to tip ends of two lead wires to be fixed to a center part of the light emitting unit 20 with an adhesive agent. A large part of such a configuration is manually provided, so that the configuration is advantageous for a case of manufacturing of a sample or small-quantity production. In a case of mass production, it is advantageous to form the sensor unit 21 on the second flexible substrate 30 as illustrated in FIGS. 4 and 6.

Embodiment 2

Figure 10:
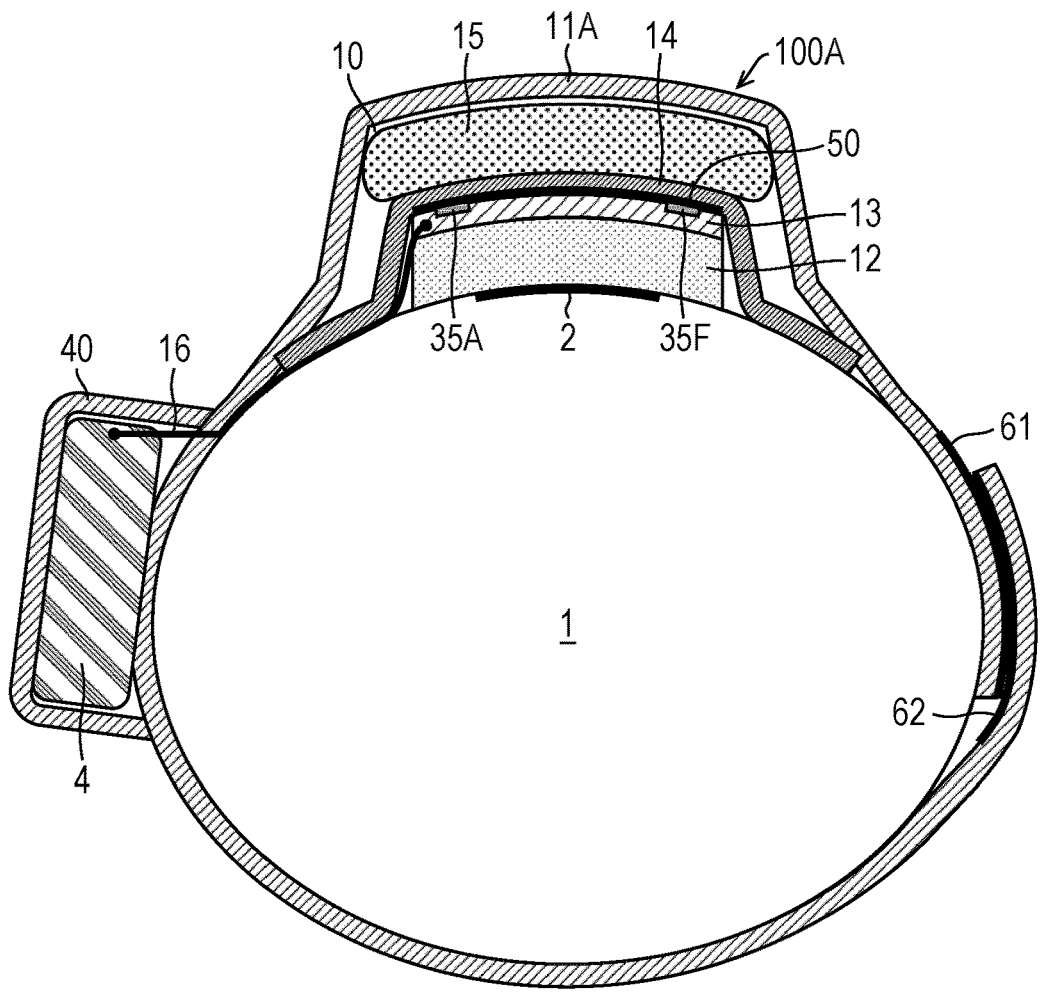
FIG. 10 is a sectional view illustrating a state where an optical treatment apparatus according to Embodiment 2 is mounted on the body.

Embodiment 2 of the invention will be described with reference to FIG. 10. FIG. 10 is a sectional view illustrating a state where an optical treatment apparatus 100A according to Embodiment 2 is mounted on the body. The optical treatment apparatus 100A illustrated in FIG. 10 and the optical treatment apparatus 100 illustrated in FIG. 1 are different in that a fixing material 11A is provided in place of the fixing material 11, and similar in other configurations.

The fixing material 11A is made from a bandage that has a band shape and an elastic property and is wound around the body 1, and when a loop fastener 61 (one of a pair of hook-and-loop fasteners) provided on a front surface (opposite side of the body 1) of one longitudinal end of the fixing material 11A and a hook fastener 62 (the other of the pair of hook-and-loop fasteners) provided on a back surface (body 1 side) of the other longitudinal end of the fixing material 11A are bonded to each other, the fixing material 11A is not allowed to be loosened.

On the back surface of the fixing material 11A, the shielding material 14 is arranged so as to completely cover the light irradiation module 13. The pocket 10 in which the cooling material 15 is able to be stored is formed between the fixing material 11A and the shielding material 14 in a state where the fixing material 11A is mounted on the body 1. On the front surface of the fixing material 11A, a power source unit pocket 40 in which the power source unit 4 is held is provided so as not to overlap with the hook fastener 62.

The present embodiment is effective, for example, for a case of a patient who may suffer from a rash due to an adhesive agent, a case where the fixing material 11A is not able to sufficiently adhere to the body 1 because of thick body hair, or a case where pain may be caused because body hair is pulled when an adhesive portion is removed from the body 1. Further, since an area of the fixing material 11A is larger than that of the fixing material 11, the power source unit pocket 40 in which the power source unit 4 is stored is easily provided, so that the patient is able to act much more freely during treatment.

Embodiment 3

Figure 11:
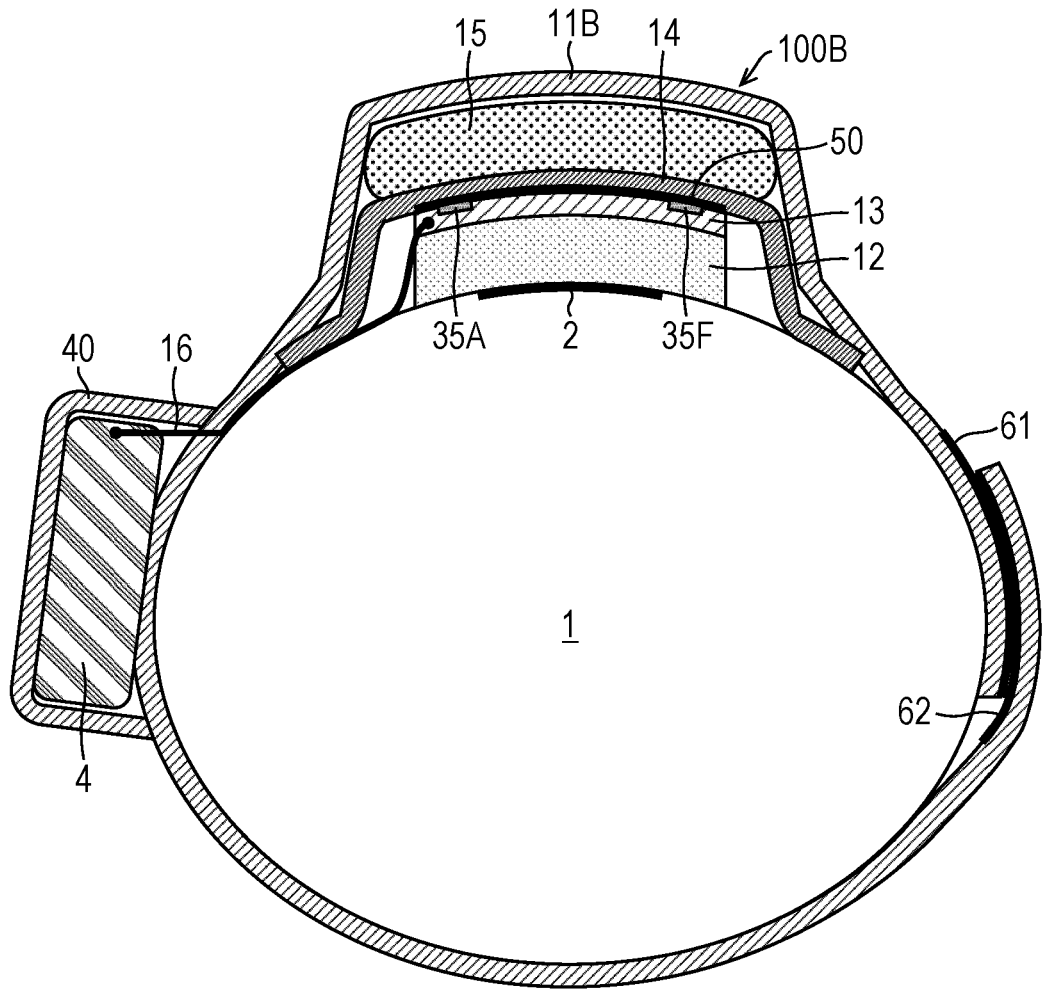
FIG. 11 is a sectional view illustrating a state where an optical treatment apparatus according to Embodiment 3 is mounted on the body.

Embodiment 3 of the invention will be described with reference to FIG. 11. FIG. 11 is a sectional view illustrating a state where an optical treatment apparatus 100B according to Embodiment 3 is mounted on the body. The optical treatment apparatus 100B illustrated in FIG. 11 and the optical treatment apparatus 100A illustrated in FIG. 10 are different in that a fixing material 11B is provided in place of the fixing material 11A, and similar in other configurations. The fixing material 11B and the fixing material 11A are different in that the shielding material 14 is formed directly adhering to one surface of the cooling material 15 instead of arranging the shielding material 14 on the fixing material 11A, and similar in other configurations.

Since the shielding material 14 adhering to the cooling material 15 contacts the terminals 35A, 35B, 35E, and 35F, similarly to Embodiment 1, the optical treatment apparatus 100B is able to check that the light irradiation module 13 is completely covered with the shielding material 14 on the basis of conductivity between one pair of terminals.

Since the shielding material 14 needs to completely cover the light irradiation module 13 and the spacer 12, the shielding material 14 needs to cover one surface of the cooling material 15 and protrude from the cooling material 15 so as to further extend to outside from an outer edge of the cooling material 15. This is because, in a case where the cooling material 15 completely covers the light irradiation module 13 and the spacer 12, the cooling material 15 protrudes from the light irradiation module 13 and the spacer 12 and directly contacts the body 1, so that the patient may feel very cold.

Since the fixing material 11B is able to be obtained with the configuration of the fixing material 11A simplified, costs are able to be reduced. On the other hand, the shielding material 14 needs to be provided on one surface of the cooling material 15 by attaching aluminum foil or the like, resulting that costs are increased. In Embodiment 1 and Embodiment 2, the shielding material 14 constitutes a part of the pocket 10 in which the cooling material 15 is held, so that the shielding material 14 needs to have a certain degree of strength. For example, mechanical strength needs to be secured, for example, by using an aluminum tape with a thickness of 50 μm to 200 μm for the shielding material 14 or backing aluminum foil with a resin sheet. However, such mechanical strength is not required in Embodiment 3, so that a thin one (with a thickness of about 25 μm) such as aluminum foil for household use is also usable as the shielding material 14 and the present embodiment is advantageous in terms of costs.

Note that, it is assumed to use the cooling material 15 in the present embodiment. Light leakage is able to be prevented in Embodiments 1 and 2 even when the cooling material 15 is not provided.

Embodiment 4

An optical treatment apparatus 100C (FIG. 1) according to Embodiment 4 of the invention and the optical treatment apparatus 100 are different in that a light irradiation module 13C is provided in place of the light irradiation module 13, and are similar in other configurations. A physical configuration of the light irradiation module 13C is basically the same as that of the light irradiation module 13 and a difference lies in how to use a current path constituted by the light irradiation module 13C and the shielding material 14.

A difference between the present embodiment and Embodiment 1 lies in that an interlocking function by which current for driving the light irradiation module 13C is cut in an abnormal case is imparted not to the power source unit 4 but to the sensor unit 21. For example, the cathode external connection unit 28C is connected to the sensor output 34A, the sensor output 34F is connected to the power source unit 4, and the anode external connection unit 28A is directly connected to the power source unit 4. Thereby, only when the terminal 35A and the terminal 35F are conductive by the conductive unit 50 of the shielding material 14, the current path is connected from the power source unit 4 to the light irradiation module 13C. That is, in the present embodiment, the current path between the terminals 35A and 35F on a back surface side of the light irradiation module 13C and the conductive unit 50 of the shielding material 14 is not used as a power source control sensor, but is used as a current switch.

In such a case, since current is ceased at a moment when pressure applied to the light irradiation module 13C by the fixing material A1 becomes lower than predetermined pressure and the shielding material 14 is removed from the light irradiation module 13C, there is advantage that current is able to be broken without fail even when the power source unit 4 malfunctions. Similarly to Embodiment 1, current is similarly not allowed to flow also in a case where mounting of the shielding material 14 is forgotten. Note that, it is certainly possible to replace the anode external connection unit 28A and the cathode external connection unit 28C.

Embodiment 5

Figure 12:
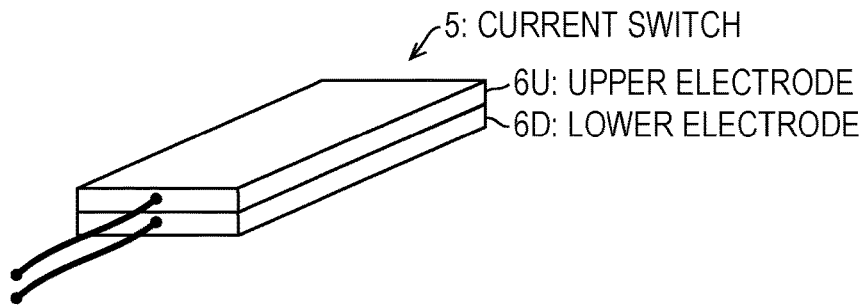
FIG. 12 is a schematic view of a current switch of an optical treatment apparatus according to Embodiment 5.
Figure 13:
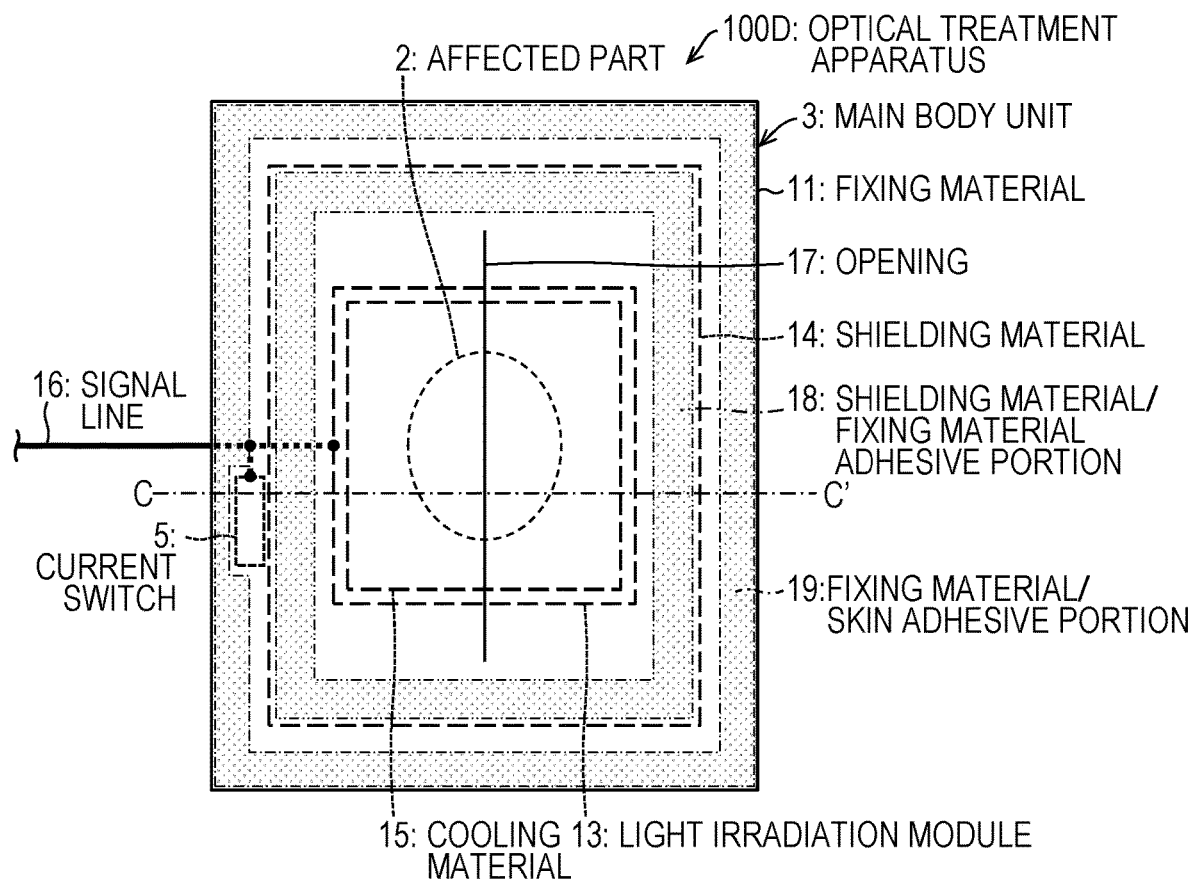
FIG. 13 is a plan view illustrating a state where the optical treatment apparatus is mounted on the body.
Figure 14:
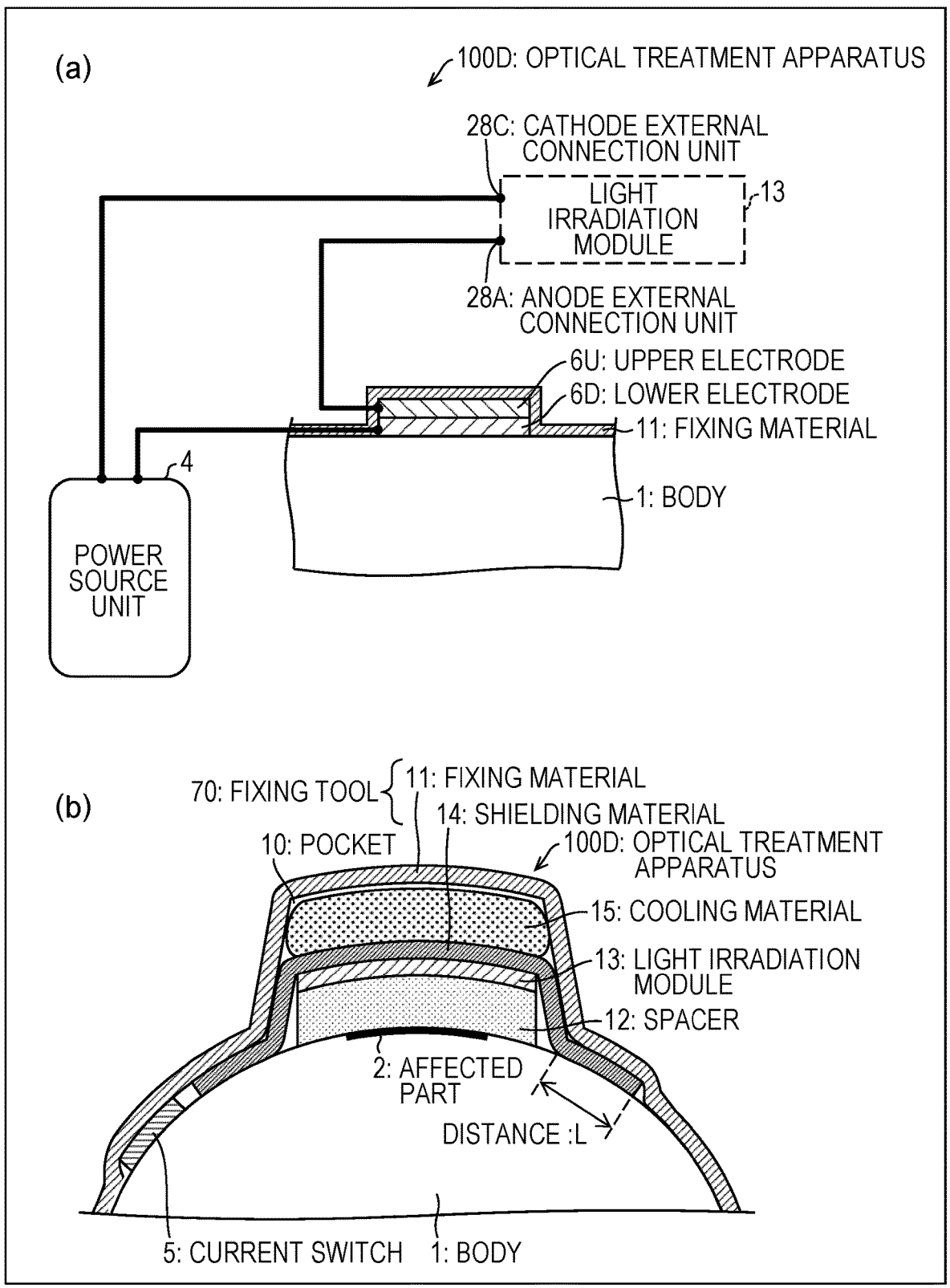
FIG. 14(a) is a schematic view of the optical treatment apparatus and FIG. 14(b) is a sectional view illustrating the state where the optical treatment apparatus is mounted on the body.

Embodiment 5 of the invention will be described with reference to FIGS. 12 to 14. FIG. 12 is a schematic view of a current switch 5 of an optical treatment apparatus 100D according to Embodiment 5. FIG. 13 is a plan view illustrating a state where the optical treatment apparatus 100D is mounted on the body. FIG. 14(a) is a schematic view of the optical treatment apparatus 100D and FIG. 14(b) is a sectional view taken along a line C-C' in FIG. 13 and illustrates the state where the optical treatment apparatus 100D is mounted on the body FIG. 14(a) specifically illustrates a part related to the current switch 5 in FIG. 14(b). The optical treatment apparatus 100D illustrated in FIGS. 14(a) and (b) and the optical treatment apparatus 100C illustrated in FIG. 1 are different in that the current switch 5 is provided, and similar in other configurations. In other words, the optical treatment apparatus 100D according to the present embodiment is different from the optical treatment apparatus 100C according to Embodiment 4 in that a current cutting function in an abnormal case is imparted to the current switch 5 beside the light irradiation module 13C. In the present embodiment, the fixing material 11 and the shielding material 14 constitute the fixing tool 70.

The current switch 5 is provided between the light irradiation module 13 and the power source unit 4, and when an upper electrode 6U and a lower electrode 6D contact, the light irradiation module 13 and the power source unit 4 are conductive.

In the current switch 5, the upper electrode 6U is provided on a surface of the fixing material 11, which is on the affected part 2 side, and the lower electrode 6D is provided on a surface of the shielding material 14, which is on the fixing material 11 side, or at a position facing the upper electrode 6U on skin around the affected part 2 that is not covered with the shielding material 14.

Specifically, the current switch 5 with a simplest form is constituted by two facing electrodes of the upper electrode 6U and the lower electrode 6D as illustrated in FIG. 12. Moreover, as illustrated in FIGS. 13 and 14, any one of the anode external connection unit 28A and the cathode external connection unit 28C is connected to the power source unit 4 and the other is connected to the upper electrode 6U. Further, the lower electrode 6D is connected to the power source unit 4. The upper electrode 6U is provided on the surface of the fixing material 11, which is on the body 1 side, and the lower electrode 6D is arranged around the affected part 2.

Thereby, when the upper electrode 6U and the lower electrode 61 are pressed by the fixing material 11, the light irradiation module 13 and the power source unit 4 become conductive. When the fixing material 11 is removed from the body 1, pressure by which the upper electrode 6U is pressed against the lower electrode 6D is weakened (pressure applied so as to press the upper electrode 6U against the lower electrode 6D becomes lower than predetermined pressure) and the upper electrode 6U and the lower electrode 6D are disconnected, so that the light irradiation module 13 and the power source unit 4 become nonconductive. Thus, in a case where the fixing material 11 is dropped out from the body 1 (when the light irradiation module 13 is removed from the affected part 2), both of the electrodes are separated and the current switch 5 is opened, so that current supply to the light irradiation module 13 is stopped. This makes it possible to immediately stop light irradiation in an abnormal case such as dropping out of the light irradiation module 13, which may be caused during phototherapy.

Each of the upper electrode 6U and the lower electrode 6D made from, for example, metal foil to one surface of which an adhesive agent is attached and which is formed with a lead wire adhering to a surface from which the metal foil is exposed. The upper electrode 6U and the lower electrode 6D are arranged so that metal foil surfaces thereof face each other. As the metal foil, for example, copper foil is usable, and one obtained by coating a copper foil surface with gold is more preferable. Aluminum foil is also usable as the upper electrode 6U and the lower electrode 6D.

Positions where the upper electrode 6U and the lower electrode 6D of the current switch 5 are placed are not limited to positions between the fixing material 11 and the body 1 and may be positions between the shielding material 14 and the fixing material 11 or between the shielding material 14 and the light irradiation module 13. In addition, in the present embodiment, the shielding material 14 is not necessarily required to include the conductive unit 50 and may be a film having an insulating property. Thus, in a case where temperature monitoring by the thermistor 32 is not necessary, the sensor unit 21 is not necessarily required to be provided.

As a modified example of the present embodiment, the conductive unit 50 of the shielding material 14 is usable as the upper electrode 6U and any one of the terminals 35A, 35B, 35E, and 35F is usable as the lower electrode 6D. As another modified example, the current switch 5 may be installed between the hook-and-loop fasteners 61 and 62 in FIG. 10. Moreover, as the current switch 5, a magnetically sensitive relay may be provided on the light irradiation module 13 and a magnet may be attached to the fixing material 11 or the shielding material 14 so that the current switch 5 is made conductive by the magnet.

The optical treatment apparatus 100D may include the power source control unit 42 (refer to FIG. 2) that instructs the current supply unit 41 to supply current and the thermistor 32, and the power source control unit 42 may have a function of stopping the supply of the current to the light irradiation module 13 in a case where an output of the thermistor 32 is greater than predetermined temperature.

Embodiment 6

Figure 15:
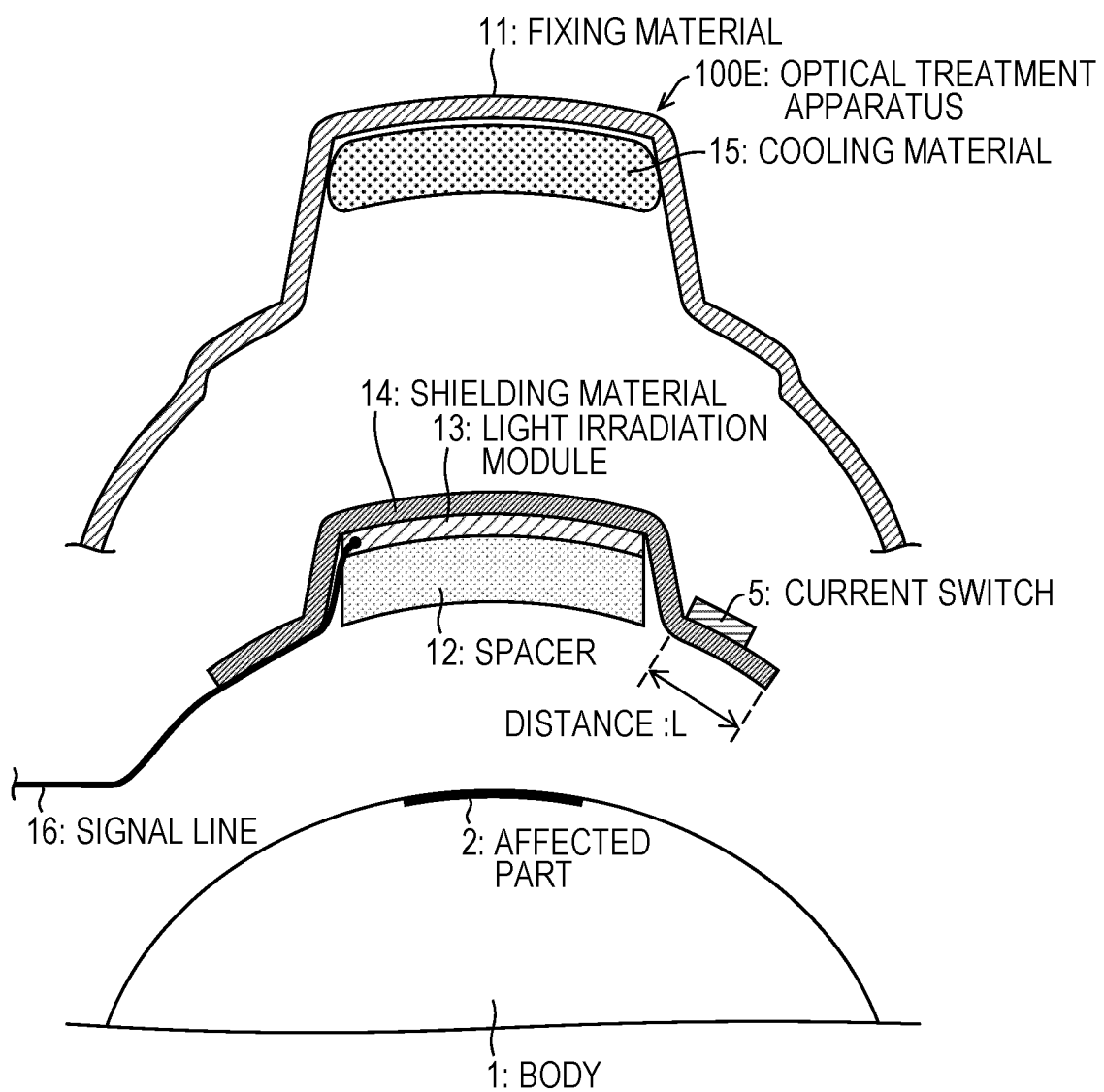
FIG. 15 is a sectional view illustrating a state where an optical treatment apparatus according to Embodiment 6 is mounted on the body, in a divided manner.

Embodiment 6 of the invention will be described with reference to FIG. 15. FIG. 15 is a sectional view illustrating a state where an optical treatment apparatus 100E according to Embodiment 6 is mounted on the body, in a divided manner. The optical treatment apparatus 100E illustrated in FIG. 15 and the optical treatment apparatus 100D illustrated in FIG. 14 are different in that the light irradiation module 13, the spacer 12, and the shielding material 14 are integrated, and similar in other configurations. Here, the integration refers to, for example, a state where the light irradiation module 13, the spacer 12, and the shielding material 14 adhere to each other and are able to be treated as one object as a whole unless being separated intentionally. Note that, the shielding material 14 covers an entire upper surface of the light irradiation module 13 in FIG. 15, but does not need to cover the entire upper surface in a case where there is no possibility that light leaks from the back surface of the light irradiation module 13.

In the optical treatment apparatus 100E, the shielding material 14 has been attached at a stage where the light irradiation module 13 is placed on the affected part 2, there is no possibility of forgetting to attach the shielding material 14.

Though safety countermeasure against an abnormal case, for example, where the light irradiation module 13 is dropped out from the fixing material 11 is required in the optical treatment apparatus 100E, such a countermeasure is taken by the current switch 5 similarly to Embodiment 5. That is, the current switch 5 is provided between the shielding material 14 and the fixing material 11 in FIG. 15. The shielding material 14 may not include the conductive unit 50, but preferably has an insulating property from a viewpoint of insulating the current switch 5.

In a state before the optical treatment apparatus 100E is mounted on the patient, the lower electrode 6D is placed in the shielding material 14, the upper electrode 6U is arranged above the lower electrode 6D, and an adhesive surface (upper surface) of the upper electrode 6U is covered with a sealing material (not illustrated). When the patient has the optical treatment apparatus 100E mounted on the affected part 2, the sealing material is removed and the fixing material 11 is put thereon. Thereby, the lower electrode 6D closely adheres to the shielding material 14 and the upper electrode 6U closely adheres to the fixing material 11. Thus, in a case where pressure by which the upper electrode 6U is pressed against the lower electrode 6D becomes lower than predetermined pressure and the fixing material 11 is dropped out in such a state, the current switch 5 is opened and supply of the current is stopped.

Note that, the current switch 5 may be provided between the body 1 and the shielding material 14 or between a front surface (affected part 2 side) of the spacer 12 and the body.

The optical treatment apparatus 100E may include the power source control unit 42 (refer to FIG. 2) that instructs the current supply unit 41 to supply current and the thermistor 32, and the power source control unit 42 may have a function of stopping the supply of the current to the light irradiation module 13 in a case where an output of the thermistor 32 is greater than predetermined temperature.

In the present embodiment, the light irradiation module 13 includes the sensor unit 21 in a case where temperature monitoring by the thermistor 32 is necessary, but may not include the sensor unit 21 in a case where the temperature monitoring is not necessary.

Embodiment 7

Figure 16:
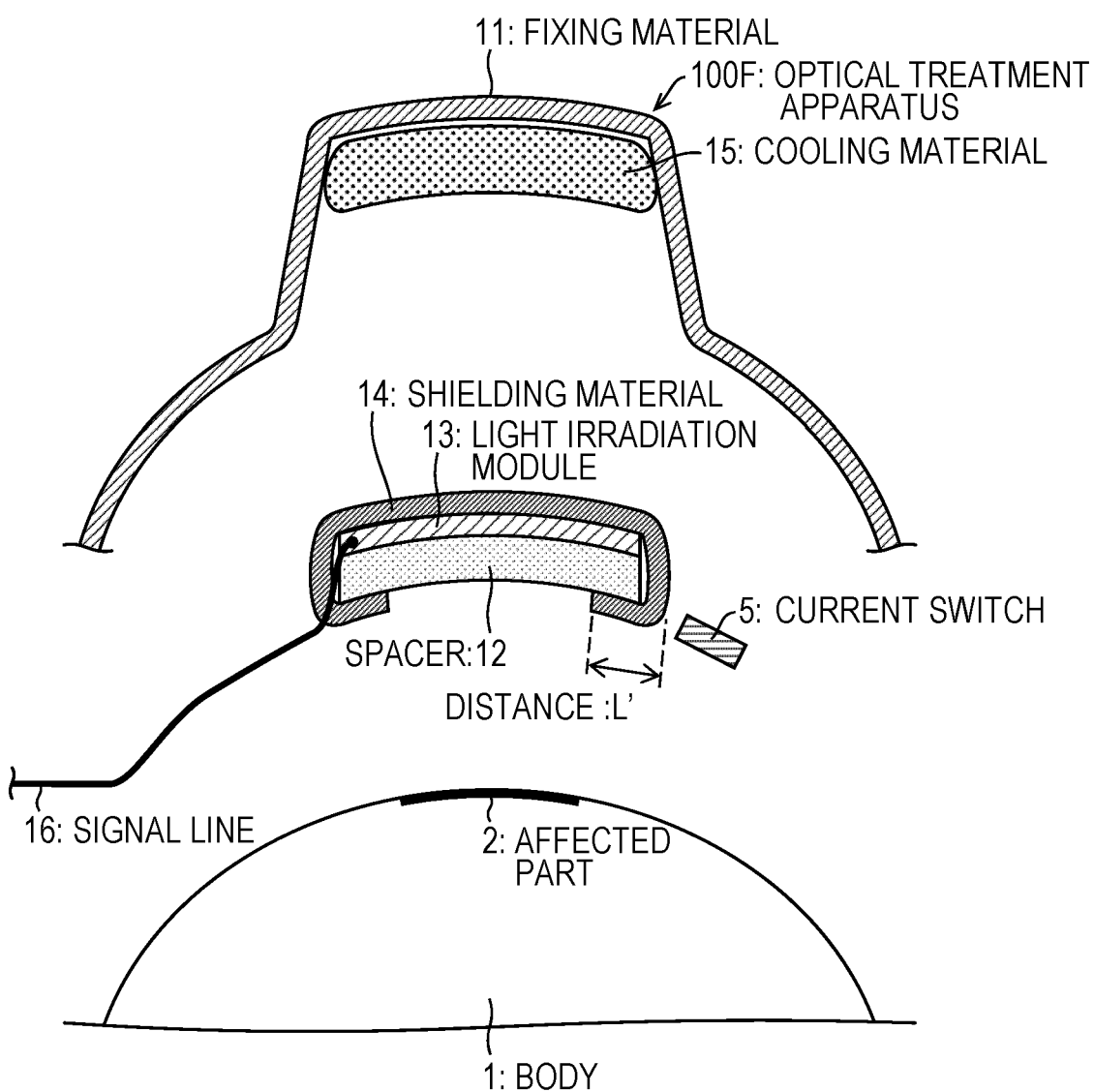
FIG. 16 is a sectional view illustrating a state where an optical treatment apparatus according to Embodiment 7 is mounted on the body, in a divided manner.

Embodiment 7 of the invention will be described with reference to FIG. 16. FIG. 16 is a sectional view illustrating a state where an optical treatment apparatus 100E according to Embodiment 7 is mounted on the body, in a divided manner. The optical treatment apparatus 100F illustrated in FIG. 16 and the optical treatment apparatus 100E illustrated in FIG. 15 are different in that the shielding material 14 extends to the surface of the spacer 12, which is on the affected part 2 side, and similar in other configurations.

Similarly to the optical treatment apparatus 100E, since the shielding material 14 is placed on the light irradiation module 13 in the optical treatment apparatus 100F, there is no possibility of forgetting to attach the shielding material 14. Further, since the shielding material 14 does not protrude from the spacer 12 and the shielding material 14, the light irradiation module 13, and the spacer 12 are integrated, an operation for mounting the optical treatment apparatus 100F onto the affected part 2 is further facilitated. There is also advantage that light irradiation to a normal part around the affected part 2 is prevented. However, since the shielding material 14 covers an outer peripheral of the affected part 2 side surface of the spacer 12, a range where the optical treatment apparats 100F is able to perform light irradiation is narrow, resulting that the present embodiment is suitable for treatment targeted for the affected part 2 with a relatively small area.

The signal line 16 passes through the shielding material 14 and connects the light irradiation module 13 and the power source unit 4. It is preferable that a part of the shielding material 14, through which the signal line 16 passes, is covered with, for example, a light-transmitting shielding material (not illustrated), such as a resin material, which contains black pigment having a light absorbing property, and does not cause light leakage. A length L' of a part of the shielding material 14, which is folded to the affected part 2 side surface of the spacer 12, is preferably at least 1.0 mm or more to prevent light leakage from the affected part 2 side surface of the spacer 12. When the length L' is less than 1.0 mm, light leakage is found. Further, for safety, it is preferable that the shielding material 14 covers the spacer 12 from an end part to a lower part and extends toward an inner side at least by 2.0 mm or more from the edge part in the lower part.

Modified Example

Though the function of stopping current in a case where a fixing function of the fixing material 11 is lost is enabled by using the current switch 5 in the optical treatment apparatus 100F, it is also possible that the function of the power source control sensor is imparted to the light irradiation module 13 and the power source unit 4 stops the current.

For example, it is possible that, in the light irradiation module 13 that includes the sensor unit 21, a pressure sensor (polymer thick film element) is installed between the terminal 35A and the terminal 35B in FIG. 6, and in a case where a pressure value of pressure related to the light irradiation module 13 and the shielding material 14 becomes lower than a predetermined value, the fixing function is regarded to be lost and current is stopped. In the light irradiation module 13 that does not include the sensor unit 21, similarly to the case of the thermistor 32, a pressure sensor may be soldered to tip ends of two lead wires and the pressure sensor may be fixed to the center part of the light emitting unit 20 with an adhesive agent.

Embodiment 8

Figure 17:
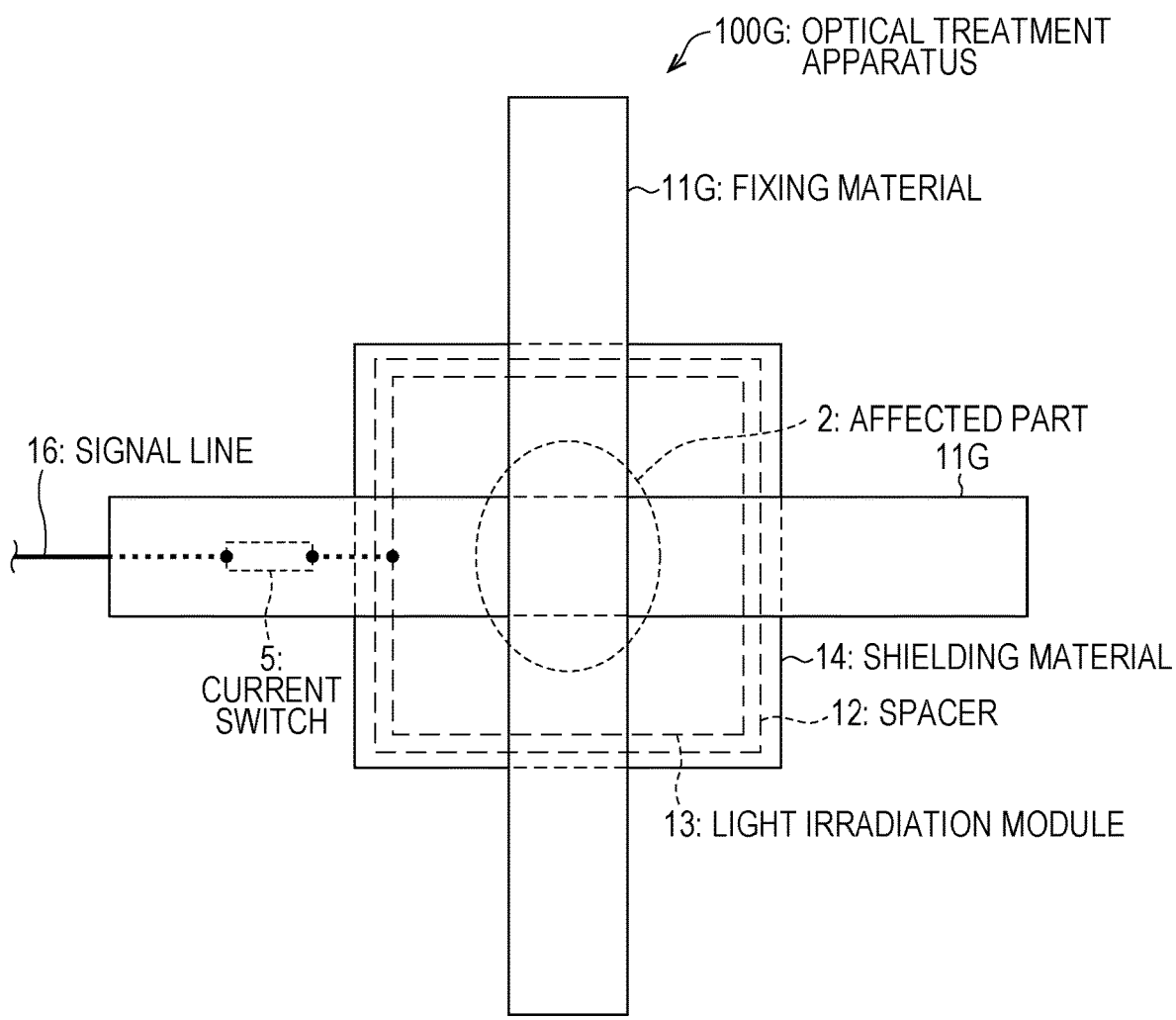
FIG. 17 is a plan view illustrating a state where an optical treatment apparatus according to Embodiment 8 is mounted on the body.

Embodiment 8 of the invention will be described with reference to FIG. 17. FIG. 17 is a plan view illustrating a state where an optical treatment apparatus 100G according to Embodiment 8 is mounted on the body. Though a case where a cooling material by the cooling material 15 or the like is not necessary is assumed in the present embodiment, the cooling material 15 may be provided.

In the optical treatment apparatus 100G illustrated in FIG. 17, the light irradiation module 13, the spacer 12, and the shielding material 14 (hereinafter, which are represented as an integrated light irradiation module) that are integrated and illustrated in FIG. 16 are held with a surgical tape which is made in a crisscross pattern. In the present embodiment, the surgical tape serves as a fixing material 11G.

A feature of the present embodiment is that the fixing material 11G does not completely cover the light irradiation module 13 or the spacer 12, compared with the optical treatment apparatus 100F. Such a form is able to be achieved because the fixing material 11G is only required to fix the integrated light irradiation module onto the affected part 2 in a case where the cooling material 15 for cooling is not necessary. In the optical treatment apparatus 100G, though the current switch 5 is used to stop the current, the power source control sensor may be provided in the light irradiation module 13 and the power source unit 4 may stop the current.

Modified Example

A modified example of Embodiment 8 of the invention will be described with reference to FIG. 18. FIG. 18 is a sectional view illustrating a state where an optical treatment apparatus 100H that is the modified example of Embodiment 8 is mounted on the body, in a divided manner. The optical treatment apparatus 100H illustrated in FIG. 18 and the optical treatment apparatus 100G illustrated in FIG. 17 are the same in that a fixing material 11H does not cover an entire upper part of the light irradiation module 13.

One or more fixing materials 11H are provided and one end of each of the fixing materials 11H is fixed in advance to a part of the surface of the shielding material 14, which is on a side opposite to that of the light irradiation module 13, at a part other than the part where the shielding material 14 extends to the surface of the spacer 12, which is on the affected part 2 side. During treatment, a bottom surface (surface on the affected part 2 side) of each of the fixing materials 11H adheres onto skin around the affected part 2, so that the fixing material 11H fixes the integrated light irradiation module onto the affected part 2. In the present embodiment, the shielding material 14 serves a part of a function of fixing the integrated light irradiation module. Thus, the shielding material 14 needs greater mechanical strength compared to those in the optical treatment apparatus 100E and the optical treatment apparatus 100G.

In the optical treatment apparatus 100H, though the current switch 5 is used to stop the current, the power source control sensor may be provided in the light irradiation module 13 and the power source unit 4 may stop the current.

Embodiment 9

Embodiment 9 of the invention will be described with reference to FIG. 19. FIG. 19 is a sectional view illustrating a state where an optical treatment apparatus 100I according to Embodiment 9 is mounted on the body, in a divided manner. In the optical treatment apparatus 100I, the integrated light irradiation module is fixed to the body by attaching an adhesive agent or a bonding agent placed on a lower surface (surface on the affected part 2 side) of the spacer 12 to the body 1 around the affected part 2. Thus, in the present embodiment, excluding the shielding material 14, the adhesive agent or the bonding agent serves as a fixing material 11I.

In FIG. 19, the fixing material 11I (adhesive agent or bonding agent) is arranged on the affected part 2 side surface of the shielding material 14 that extends to the affected part 2 side of the spacer 12, but may be arranged on a part of the lower surface of the spacer 12. When the fixing material 11I is transparent, the fixing material 11I may be arranged on an entire bottom surface of the spacer 12.

In the present embodiment, when the adhesive agent or the bonding agent serving as the fixing material 11I is attached in advance to at least a part of a lower surface of the integrated light irradiation module and the fixing material 11I is covered with releasing paper, the fixing material 11I is able to be immediately attached to the affected part 2 by removing the releasing paper.

In the optical treatment apparatus 100I, the power source control sensor is mounted in the light irradiation module 13 and the power source unit 4 stops the current on the basis of a detection result, of the power source control sensor. The optical treatment apparatus 100I uses an acceleration sensor as the power source control sensor. Since the light irradiation module 13 suddenly moves when the fixing function is lost, the acceleration sensor is mounted in the light irradiation module 13 and the acceleration sensor acquires an acceleration change of the light irradiation module 13, so that it is possible to detect loss of the fixing function.

In the optical treatment apparatus 100I, as the power source control sensor that stops the current, an absolute pressure sensor (MEMS pressure sensor) is also usable in addition to the acceleration sensor. When the fixing function is lost and the light irradiation module 13 is dropped, an altitude is reduced by several tens of centimeters, so that, by detecting a pressure change due to the altitude change, the loss of the fixing function is able to be detected.

In the optical treatment apparatus 100I, the light irradiation module 13 is not pressed from above, so that it is not preferable to use conduction upon contact between a terminal and the conductive unit 50 or a pressure sensor in order to stop current.

Instead of imparting the sensor function to the light irradiation module 13, the current switch 5 may be installed on the lower surface of the spacer 12. In the present embodiment, treatment is able to be started only by attaching the integrated light irradiation module with use of the adhesive agent or the like onto skin around the affected part 2 so as to cover the affected part 2, so that there is advantage that operation efficiency is able to be improved at a medical site.

Modified Example

Figure 20:
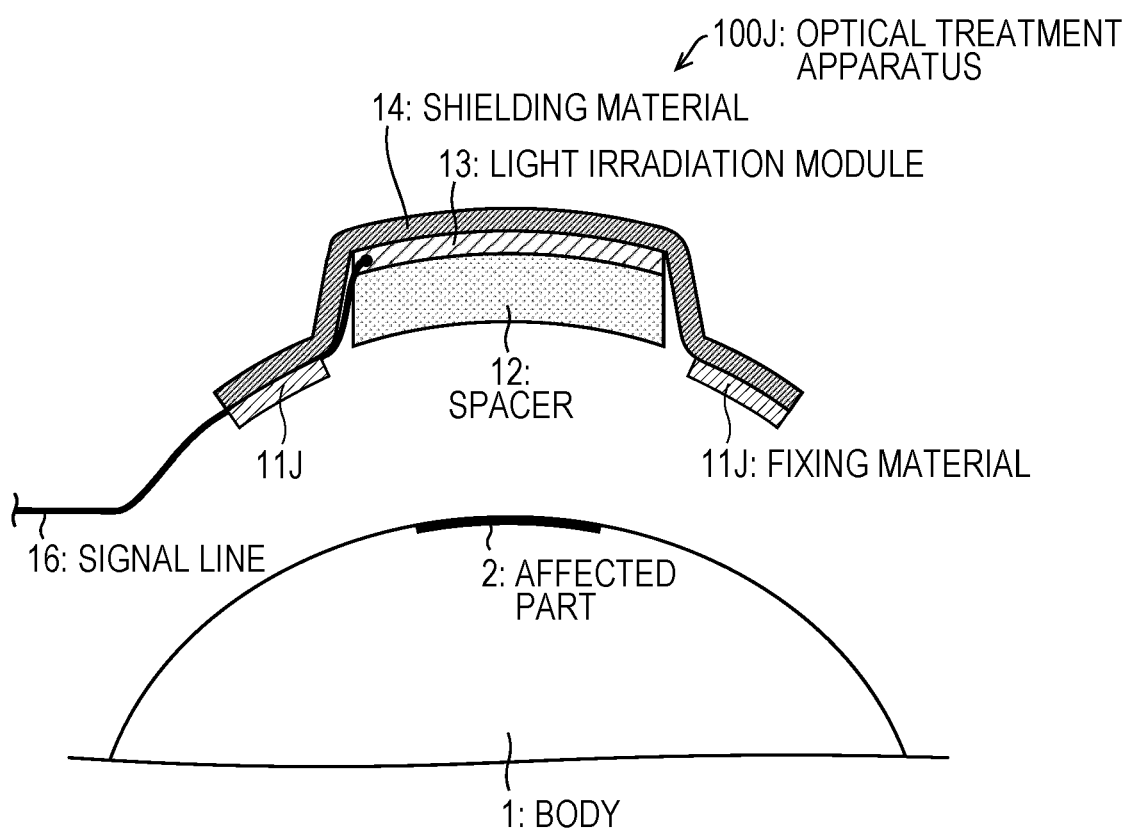
FIG. 20 is a sectional view illustrating a state where a modified example of the optical treatment apparatus is mounted on the body, in a divided manner.

A modified example of Embodiment 9 of the invention will be described with reference to FIG. 20. FIG. 20 is a sectional view illustrating a state where an optical treatment apparatus 100J that is the modified example of Embodiment 9 is mounted on the body, in a divided manner. The optical treatment apparatus 100J illustrated in FIG. 10 and the optical treatment apparatus 100I illustrated in FIG. 19 are different in that the end of the shielding material 14 covers not the bottom surface of the spacer 12 but skin outside the light irradiation module 13 or the spacer 12. An adhesive agent or a bonding agent serving as a fixing material 11J is placed on a surface of the end of the shielding material 14, which is on the affected part 2 side. In the optical treatment apparatus 100J, the bottom surface of the spacer 12 is all opened, so that treatment is able to be performed for a wider area. In this manner, in a case where there is no possibility that the fixing material 11J overlaps with the affected part 2, it is preferable that the fixing material 11J is not transparent with respect to therapeutic light in order to prevent light leakage to outside.

CONCLUSION

An optical treatment apparatus (100, 100A, 100B, 100C, 100D, 100E, 100F, 100G) according to an aspect 1 of the invention includes: a power source unit (4); a light irradiation module (13, 13C) that irradiates a target (affected part 2) with light when current is supplied from the power source unit; a transparent spacer (spacer 12) that is positioned between the light irradiation module and the target; a fixing material (11, 11A, 11B, 11G) that applies predetermined pressure so as to press the light irradiation module against the transparent spacer and fixes the light irradiation module at an installation position; and a light shielding unit (shielding material 14) that is provided between the light irradiation module and the fixing material and covers the light irradiation module, in which, in a case where pressure applied by the fixing material becomes lower than the predetermined pressure, the supply of the current is stopped.

According to the aforementioned configuration, since the fixing material applies the predetermined pressure to the light irradiation module to press the light irradiation module against the transparent spacer so that the light irradiation module is fixed at the installation position, the light irradiation module is able to be fixed to the target without fixing the light irradiation module and the fixing material. Thus, the light irradiation module and the fixing material are able to be separated and only the light irradiation module is able to be replaced in accordance with a size of the target.

The transparent spacer that transmits light radiated from the light irradiation module is provided between the light irradiation module and the target. This makes it possible to prevent heat generated in the light irradiation module from being directly transferred to the target, so that a large-sized cooling device is not necessary. Further, a cooling water circulation device or the like does not need to be installed, so that a patient is able to be prevented from being restrained during the treatment.

The light shielding unit is between the light irradiation module and the fixing material. Thus, the light shielding unit is fixed by the fixing material and the light irradiation module is covered with the light shielding unit, thus making it possible to shield light, which is radiated to the target by the light irradiation module and leaks from a gap between the light irradiation module and a body to outside, to an almost negligible degree.

Further, the current supplied to the light irradiation module is stopped in a case where the pressure applied by the fixing material becomes lower than the predetermined pressure. Thus, for example, in a case where fixation by the fixing material is loosened, the supply of the current is stopped and light irradiation is stopped, thus making it possible to prevent light from leaking to outside.

Accordingly, the aforementioned configuration enables light irradiation therapy that allows reduction of burden on a patient or a medical practitioner, and that is safe and requires less labor.

An optical treatment apparatus (100H, 100I, 100J) according to an aspect 2 of the invention includes: a power source unit (4); a light irradiation module (13) that irradiates a target (affected part 2) with light when current is supplied from the power source unit; a transparent spacer (spacer 12) that is positioned between the light irradiation module and the target; a fixing material (11H, 11I, 11J) that fixes the light irradiation module and the transparent spacer to be on the target; and a light shielding unit (shielding material 14) that covers the light irradiation module and the transparent spacer, in which, in a case where the light irradiation module is removed from the target, the supply of the current is stopped.

According to the aforementioned configuration, the transparent spacer that transmits light radiated from the light irradiation module is provided between the light irradiation module and the target. This makes it possible to prevent heat generated in the light irradiation module from being directly transferred to the target, so that a large-sized cooling device is not necessary. Further, cooling water circulation device or the like does not need to be installed, so that a patient is able to be prevented from being restrained during the treatment.

Since the light irradiation module and the transparent spacer are covered with the light shielding unit, it is possible to shield light, which is radiated to the target by the light irradiation module and leaks from a gap between the light irradiation module and a body or from the transparent spacer to outside, to an almost negligible degree.

Further, supply of the current to the light irradiation module is stopped in a case where the light irradiation module is removed from the target. Thus, for example, in a case where fixation of the fixing material is loosened and the light irradiation module is removed from the target, light irradiation is stopped, thus making it possible to prevent light from leaking to outside.

Accordingly, the aforementioned configuration enables light irradiation therapy that allows reduction of burden on a patient or a medical practitioner, and that is safe and requires less labor.

(100, 100A, 100B, 100C, 100F, 100G, 100H, 100I, 100J) according to an aspect 3 of the invention further includes a sensor (power source control sensor), in which the power source unit (4) stops the supply of the current in response to a signal from the sensor, in the aspect 1 or 2.

According to the aforementioned configuration, in a treatment site, treatment is able to be started only by fixing the light irradiation module, the spacer, and the shielding material to the affected part by the fixing material and connecting the light irradiation module and the power source unit by a signal line, thus making it possible to minimize labor of a medical practitioner.

(100D, 100E, 100F, 100G, 100H, 100I, 100J) according to an aspect 4 of the invention further includes a current switch (5) between the light irradiation module (13) and the power source unit (4), in which, when the current switch is opened, the supply of the current is stopped, in the aspect 1 or 2.

According to the aforementioned configuration, the power source unit does not need to have a function of breaking the current in response to a signal of the sensor, so that a structure is able to be simplified and costs of the power source unit are able to be reduced. Moreover, malfunction, such as loss of a current stopping function, caused by an erroneous operation of the sensor or an erroneous operation of the power source unit does not occur.

In (100, 100A, 100B, 100C, 100D, 100E) according to an aspect 5 of the invention, in a case where existence of the light shielding unit (shielding material 14) is not detected, the supply of the current is stopped, in the aspects 1 to 4.

According to the aforementioned configuration, in a case where the shielding material is not placed, the current is broken so that light is not radiated. Thereby, in a case where the shielding material is provided separately from the light irradiation module and the spacer, it is possible to prevent a risk that a patient or a medical practitioner sees strong light because of forgetting to place the shielding material during treatment.

(100, 100A, 100B, 100C) according to an aspect 6 of the invention further includes: at least one pair of electrodes (terminals 35A, 35F) provided on a surface of the light irradiation module (13, 13C), which is on a side of the light shielding unit (shielding material 14); and a conductive unit (50) that is provided at a position facing the one pair of electrodes on a surface of the light shielding unit, which is on a side of the light irradiation module, in which in a case where the at least one pair of electrodes is nonconductive, the supply of the current to the light irradiation module is stopped, in the aspects 1 to 5.

According to the aforementioned configuration, unless the light irradiation module and the light shielding unit contact, the light irradiation module does not radiate light. That is, the light irradiation module radiates light only in a state of being covered with the light shielding unit. Thus, for example, even in a case where the fixing material is removed and the light irradiation module and the light shielding unit are separated, light irradiation is stopped, thus making it possible to prevent light from leaking to outside.

According to the aforementioned configuration, it is also possible that whether or not the one pair of electrodes and the conductive unit are conductive is detected and the power source unit stops the current. That is, use as the sensor of the aspect 3 is possible. It is also possible to use the one pair of electrodes and the conductive unit as the current switch of the aspect 4 to break the current. The present configuration has advantage that a sensor, such as a pressure sensor or an acceleration sensor, which has an advanced function is not necessary, manufacturing is able to be performed with electrodes and a conductor which are very simple and low-cost parts, and mass production is able to be achieved by using a thin film process.

In the optical treatment apparatus (100D, 100E, 100F, 100G, 100H) according to an aspect 7 of the invention, the current switch (5) includes an upper electrode (6U) and a lower electrode (6D), and the upper electrode is provided on a surface of the fixing material (11) which is on a side of the target (affected part 2), and the lower electrode is provided at a position facing the upper electrode on a surface of the light shielding unit, which is on a side of the fixing material, or around the target, in the aspect 4.

According to the aforementioned configuration, in such an abnormal case that the light irradiation module is dropped out from the fixing material, the upper electrode and the lower electrode are separated and conductivity between the light irradiation module and the power source unit is cut. This makes it possible to stop the supply of the current to the light irradiation module and stop light irradiation in the abnormal case.

The present configuration has advantage that a sensor, such as a pressure sensor or an acceleration sensor, which has an advanced function is not necessary, and manufacturing is able to be performed with electrodes which are very simple and low-cost parts.

In the optical treatment apparatus (100, 100A, 100B, 100C, 100D, 100E, 100F, 100G, 100H, 100I, 100J) according to an aspect 8 of the invention, it is preferable that the light irradiation module (13, 13C) includes a temperature sensor (thermistor 32), and in a case where the temperature sensor detects temperature higher than predetermined temperature, the supply of the current to the light irradiation module is stopped, in the aspects 1 to 7.

According to the aforementioned configuration, light irradiation of the light irradiation module is able to be stopped in a case where the light irradiation module has high temperature.

In the optical treatment apparatus (100, 100A, 100B, 100C, 100D, 100E, 100J) according to an aspect 9 of the invention, in a state where the light irradiation module is fixed by the fixing material (11), the light shielding unit extends to an outer side by at least 5 mm or more from an outer edge of the transparent spacer (spacer 12) or the light irradiation module, in the aspects 1 to 8.

According to the aforementioned configuration, the light shielding unit is able to reliably cover the transparent spacer or the light irradiation module and reliably prevent light leakage. Light irradiation is able to be performed for an entire lower surface of the transparent spacer, thus enabling dealing with an affected part with a wider area.

In the optical treatment apparatus (100F, 100G, 100H, 100I) according to an aspect 10 of the invention, the light shielding unit (shielding material 14) covers the transparent spacer (spacer 12) from an end part to a lower part, and extends toward an inner side at least by 2.0 mm or more from the end part in the lower part, in the aspect 1, 2, 3, 4, 5, 6, 7, or 8.

According to the aforementioned configuration, since the light irradiation module, the transparent spacer, and the shielding material are able to be integrated, forgetting to attach the shielding material is not caused. Compared with a case where they are installed separately, labor required for installation on the affected part is able to be reduced.

A fixing tool (70) according to an aspect 11 of the invention includes: a fixing material (fixing material 11) that applies predetermined pressure to a light irradiation module (13) that irradiates a target (affected part 2) with light; and a light shielding unit (shielding material 14) that covers the light irradiation module, in which the fixing material includes a convex portion (111) on an opposite side of the target, a space (pocket 10) is formed by the light shielding unit and the convex portion, and the convex portion is provided with an opening (17) that is openable or closeable.

According to the aforementioned configuration, the light irradiation module is fixed when the predetermined pressure is applied by the fixing material. Thus, various light irradiation modules are able to be fixed regardless of shapes or sizes of light irradiation modules.

Since the light shielding unit that covers the light irradiation module is provided, it is possible to shield light, which is radiated to the target by the light irradiation module and leaks from a gap between the light irradiation module that covers the target and a body to outside, to an almost negligible degree.

By the convex portion, the space having the opening that is openable or closeable is formed between the light shielding unit and the fixing material, so that a cooling material or the like is able to be inserted into the space and a temperature rise of the light irradiation module is able to be suppressed. Since heat generation from the light irradiation module is able to be suppressed by putting the cooling material in the space, a cooling device is not necessary. Thereby, a cooling water circulation device or the like does not need to be installed, so that a patient is able to be prevented from being restrained during treatment.

Accordingly, the aforementioned configuration enables light irradiation therapy that allows reduction of burden on a patient or a medical practitioner, and that is safe and requires less labor.

In the fixing tool (70) according to an aspect 12 of the invention, it is preferable that the fixing material (fixing material 11) has an elastic property in the aspect 11.

According to the aforementioned configuration, the fixing material has the elastic property and is thus able to flexibly correspond to various shapes.

The invention is not limited to each of the embodiments described above, and may be modified in various manners within the scope indicated in the claims and an embodiment achieved by appropriately combining technical means disclosed in each of different embodiments is also encompassed in the technical scope of the invention. Further, by combining the technical means disclosed in each of the embodiments, a new technical feature may be formed.

REFERENCE SIGNS LIST 1 body
2 affected part (target)
4 power source unit
5 current switch (sensor)
6U upper electrode
6D lower electrode
10 pocket (space)
11, 11A, 11B, 11G, 11H fixing material (pressure applying member)
11I, 11J fixing material (adhesive agent or bonding agent)
12 spacer (transparent spacer)
13, 13C light irradiation module
14 shielding material (shielding unit)
17 opening
32 thermistor (temperature sensor)
35A, 35B, 35E, 35F terminal (electrode)
41 current supply unit
42 power source control unit
50 conductive unit (sensor)
70 fixing tool
100, 100A, 100B, 100C, 100D, 100E, 100F, 100G, 100H, 100I, 100J light irradiation module
111 convex portion

The invention claimed is:

1. An optical treatment apparatus comprising:
a power source unit;
a light irradiation module that irradiates a target with light when current is supplied from the power source unit;
a transparent spacer that is positioned between the light irradiation module and the target;
a fixing material that applies predetermined pressure so as to press the light irradiation module against the transparent spacer and fixes the light irradiation module at an installation position;
a light shielding unit that is provided between the light irradiation module and the fixing material and covers the light irradiation module;
at least one pair of electrodes connected to the power source unit and provided on a surface of the light irradiation module, which is on a side of the light shielding unit; and
a conductive unit that is provided at a position facing the at least one pair of electrodes on a surface of the light shielding unit, which is on a side of the light irradiation module, wherein
in a case where the power source unit detects that the at least one pair of electrodes is nonconductive, the power source unit stops the supply of the current to the light irradiation module.

2. The optical treatment apparatus according to claim 1, wherein
the light irradiation module includes a temperature sensor, and
in a case where the temperature sensor detects temperature higher than predetermined temperature, the supply of the current to the light irradiation module is stopped.

3. The optical treatment apparatus according to claim 1, wherein, in a state where the light irradiation module is fixed by the fixing material, the light shielding unit covers a whole of the transparent spacer and a minimum distance from an end of the transparent spacer to an end of the shielding unit is at least 5 mm or more.

4. The optical treatment apparatus according to claim 1, wherein the light shielding unit covers the transparent spacer and turns below the transparent spacer at an entire periphery of the transparent spacer, and at a bottom of the transparent spacer a minimum distance between an end of the light shielding unit and an edge of the transparent spacer is at least 2.0 mm or more.

5. An optical treatment apparatus comprising:
a power source unit;
a light irradiation module that irradiates a target with light when current is supplied from the power source unit;
a transparent spacer that is positioned between the light irradiation module and the target;
a fixing material that applies predetermined pressure so as to press the light irradiation module against the transparent spacer and fixes the light irradiation module at an installation position; and
a light shielding unit that is provided between the light irradiation module and the fixing material and covers the light irradiation module, wherein
the light irradiation module has a plurality of light emitting elements uniformly arranged on a flexible substrate and a pressure sensor connected to the power source unit,
an area of the transparent spacer is equal to or greater than an area of the light irradiation module, and
in a case where the pressure sensor senses that pressure applied by the fixing material becomes lower than the predetermined pressure, the power source unit stops the supply of the current, and
in a case where existence of the light shielding unit is not detected, the supply of the current is stopped.

6. The optical treatment apparatus according to claim 5, further comprising a sensor, wherein the power source unit stops the supply of the current in response to a signal from the sensor.

7. The optical treatment apparatus according to claim 5, further comprising a current switch between the light irradiation module and the power source unit, wherein, when the current switch is opened, the supply of the current is stopped.

8. The optical treatment apparatus according to claim 5, wherein
the light irradiation module includes a temperature sensor,
the temperature sensor measures temperature of the light irradiation module, and
in a case where the temperature sensor detects temperature higher than predetermined temperature, the supply of the current to the light irradiation module is stopped.

9. The optical treatment apparatus according to claim 5, wherein, in a state where the light irradiation module is fixed by the fixing material, the light shielding unit covers an whole of the transparent spacer and a minimum distance from an end of the transparent spacer to an end of the shielding unit is at least 5 mm or more.

10. The optical treatment apparatus according to claim 5, wherein the light shielding unit covers the transparent spacer and turns below the transparent spacer at entire periphery of the transparent spacer, and at a bottom of the transparent spacer a minimum distance between an end of the light shielding unit and an edge of the transparent spacer is at least by 2.0 mm or more.

11. An optical treatment apparatus comprising:
a power source unit;
a light irradiation module that irradiates a target with light when current is supplied from the power source unit;
a transparent spacer that is positioned between the light irradiation module and the target;
a fixing material that applies predetermined pressure so as to press the light irradiation module against the transparent spacer and fixes the light irradiation module at an installation position; and
a light shielding unit that is provided between the light irradiation module and the fixing material and covers the light irradiation module; and
a current switch between the light irradiation module and the power source unit, wherein
the light irradiation module has a plurality of light emitting elements uniformly arranged on a flexible substrate,
an area of the transparent spacer is equal to or greater than an area of the light irradiation module,
in a case where pressure applied by the fixing material becomes lower than the predetermined pressure, the current switch opens to stop the supply of the current,
the current switch includes an upper electrode and a lower electrode, and
the upper electrode is provided on a surface of the fixing material, which is on a side of the target, and the lower electrode is provided at a position facing the upper electrode on a surface of the light shielding unit, which is on a side of the fixing material, or around the target.

12. An optical treatment apparatus comprising:
a power source unit;
a light irradiation module that irradiates a target with light when current is supplied from the power source unit;
a transparent spacer that is positioned between the light irradiation module and the target;
a fixing material that fixes the light irradiation module and the transparent spacer to be on the target; and
a light shielding unit that covers the light irradiation module and the transparent spacer, wherein
the light irradiation module has a plurality of light emitting elements uniformly arranged on a flexible substrate and a power source control sensor connected to the power source unit,
an area of the transparent spacer is equal to or greater than an area of the light irradiation module, and
in a case where the power source control sensor senses that the light irradiation module is removed from the target, the power source unit stops the supply of the current, and
in a case where existence of the light shielding unit is not detected, the supply of the current is stopped.

13. The optical treatment apparatus according to claim 12, further comprising a sensor, wherein the power source unit stops the supply of the current in response to a signal from the sensor.

14. The optical treatment apparatus according to claim 12, further comprising a current switch between the light irradiation module and the power source unit, wherein, when the current switch is opened, the supply of the current is stopped.

15. The optical treatment apparatus according to claim 12, wherein
the light irradiation module includes a temperature sensor,
the temperature sensor measures temperature of the light irradiation module, and
in a case where the temperature sensor detects temperature higher than predetermined temperature, the supply of the current to the light irradiation module is stopped.

16. The optical treatment apparatus according to claim 12, wherein, in a state where the light irradiation module is fixed by the fixing material, the light shielding unit covers a whole of the transparent spacer and a minimum distance from an end of the transparent spacer to an end of the shielding unit is at least 5 mm or more.

17. The optical treatment apparatus according to claim 12, wherein the light shielding unit covers the transparent spacer and turns below the transparent spacer at an entire periphery of the transparent spacer, and at a bottom of the transparent spacer a minimum distance between an end of the light shielding unit and an edge of the transparent spacer is at least 2.0 mm or more.

18. An optical treatment apparatus comprising:
a power source unit;
a light irradiation module that irradiates a target with light when current is supplied from the power source unit;
a transparent spacer that is positioned between the light irradiation module and the target
a fixing material that fixes the light irradiation module and the transparent spacer to be on the target; and
a light shielding unit that covers the light irradiation module and the transparent spacer;
a current switch between the light irradiation module and the power source unit, wherein
the light irradiation module has a plurality of light emitting elements uniformly arranged on a flexible substrate,
an area of the transparent spacer is equal to or greater than an area of the light irradiation module, and
in a case where the light irradiation module is removed from the target, the current switch opens to stop the supply of the current,
the current switch includes an upper electrode and a lower electrode, and
the upper electrode is provided on a surface of the fixing material, which is on a side of the target, and the lower electrode is provided at a position facing the upper electrode on a surface of the light shielding unit, which is on a side of the fixing material, or around the target.

* * * * *